United States Patent
Landro et al.

(10) Patent No.: US 6,994,956 B2
(45) Date of Patent: Feb. 7, 2006

(54) METHOD FOR ASSAYING ENZYME ACTIVITY

(75) Inventors: James A. Landro, Cheshire, CT (US); David G. Osterman, Glastonbury, CT (US); Walter Pickett, Madison, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 10/911,242

(22) Filed: Aug. 4, 2004

(65) Prior Publication Data

US 2005/0064531 A1   Mar. 24, 2005

Related U.S. Application Data

(60) Provisional application No. 60/492,763, filed on Aug. 4, 2003.

(51) Int. Cl.
*C12Q 1/00*   (2006.01)

(52) U.S. Cl. .......................................................... 435/4

(58) Field of Classification Search ................... 435/4, 435/15, 25, 963
See application file for complete search history.

(56) References Cited

U.S. PATENT DOCUMENTS

| | | | | |
|---|---|---|---|---|
| 4,563,305 A | * | 1/1986 | Ryan et al. | 530/331 |
| 5,785,992 A | * | 7/1998 | Ansell et al. | 424/450 |
| 2003/0203411 A1 | * | 10/2003 | Sabbadini et al. | 435/7.2 |
| 2004/0018487 A1 | * | 1/2004 | Lu et al. | 435/5 |
| 2005/0026235 A1 | * | 2/2005 | Graham | 435/21 |

* cited by examiner

*Primary Examiner*—Ralph Gitomer
(74) *Attorney, Agent, or Firm*—Susan M. Pellegrino

(57) ABSTRACT

The present invention relates to methods for assessing enzyme activity utilizing a phase partition system. In addition, the present invention also relates to methods for screening and identifying compounds that may be used, for example, for the treatment of diabetes, diabetes-related disorders, obesity, cardiovascular disease, cancer, and other diseases or disorders, using this phase partition system.

24 Claims, 14 Drawing Sheets

METHOD FOR ASSAYING ENZYME ACTIVITY

This application claims benefit of U.S. Provisional Application Ser. No. 60/492,763, filed on Aug. 4, 2003, the contents of which are incorporated herein by reference in their entirety.

FIELD OF THE INVENTION

The present invention relates to methods for assessing enzyme activity utilizing a phase partition system. In addition, the present invention also relates to methods for screening and identifying compounds that may be used, for example, for the treatment of diabetes, diabetes-related disorders, obesity, cardiovascular disease, cancer, and other diseases or disorders, using this phase partition system.

BACKGROUND OF THE INVENTION

The pharmaceutical industry has focused on the identification of small molecule compounds that modulate (e.g., block, reduce, or enhance) specific steps in biological pathways. Lead Discovery, the process of identifying, cloning, expressing, and running a high throughput screen (HTS) for the purpose of identifying lead chemical matter as a starting point for development of therapeutic drugs plays a key role in drug discovery. Historically, this has meant a focus on those targets that are considered readily amenable to HTS. A test or assay for HTS must measure a relevant activity of the target, produce a robust signal for that activity, be readily assembled from commercial and/or in-house prepared reagents, and entail the minimum possible sequence of physical steps involving addition or sampling of the test reagents/mixture. In this way, a large volume of samples may be evaluated in a short period of time, and enables for automation of steps.

In general, because of time and labor constraints for assay methods, lipid metabolism proteins have not been assayed by HTS. However, because of the diverse array of chemical matter within HTS compound files having pharmacological potential for lipid metabolism targets, there exists a distinct need to prosecute these targets through HTS.

Lipids play an indispensable role in cell structure, metabolism, and cell signaling. For example, fatty acids and triacylglycerols are the major storehouse of metabolic energy. Enzymes that digest, oxidize, and synthesize these energy storage forms are potential therapeutic intervention points for drug discovery, for example, in the areas of cancer, obesity, cardiovascular, and diabetes research. In addition to their metabolic role, phospholipids play key roles in signal transduction pathways, and biological macromolecules that control phospholipid metabolism are also potential drug discovery targets. Traditional assay methods for lipid metabolism targets, including thin layer chromatography (TLC) and high-pressure liquid chromatography (HPLC), are labor- and time-intensive. Thus, there is a need in the pharmaceutical industry to develop methods to screen lipid metabolism targets that are efficient and cost-effective.

SUMMARY OF THE INVENTION

The present invention relates to methods for measuring enzyme activity comprising the steps of combining enzyme and substrate(s); incubating the reaction mix; adding a phase-partition fluid (e.g., phase-partition scintillation fluid); and detecting enzyme activity. If appropriate, the reaction may be terminated by acidification of the reaction mix. In one embodiment of the invention, the reaction may be conducted in a single reaction vessel (e.g., organic resistant multiwell plate). In another embodiment, the methods of the present invention may be used for high throughput screens.

As an example, these methods may be used to assess the activity of the following enzymes: fatty acid synthase; acetyl CoA carboxylase; diacylglycerol acetyltransferase; farnesyl diphosphate synthase; glycerol-3-phosphate O-acyltransferase; carnitine O-palmitoyltransferase 1; serine C-palmitoyltransferase; and phospholipase C gamma.

In a further embodiment, the methods of the present invention may used to identify compounds that modulate enzyme activity. In another embodiment of the invention, compounds identified by these methods may be used, for example, for the treatment of diabetes, diabetes-related disorders, obesity, cardiovascular disease, and cancer.

DESCRIPTION OF THE INVENTION

Figure 1:
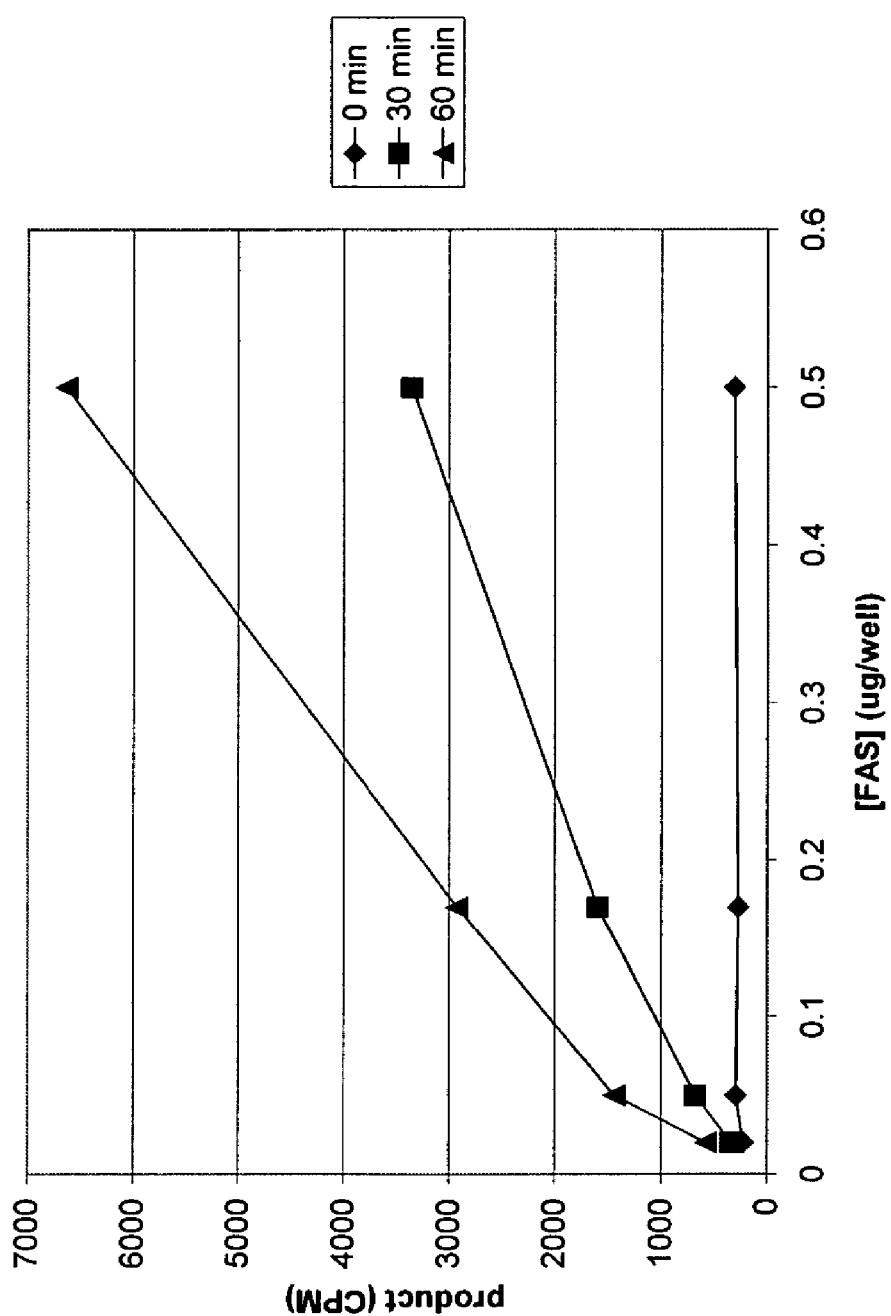
FIG. 1. Time course and protein dependence of fatty acid synthase (FAS)-produced product partitioning into the organic phase. FAS was incubated at varying concentrations and times at room temperature with 400 $\mu$M NADPH, 100 $\mu$M acetyl-CoA, and 20 $\mu$M malonyl-CoA (0.02 $\mu$Ci [malonyl-2-$^{14}$C]-CoA) in buffer containing 50 mM MOPS (pH 6.8), 5 mM DTT, 1 mM EDTA, and 0.03% BSA in a total volume of 100 $\mu$L. The reaction was terminated by the addition of 10 $\mu$L of 10 N acetic acid, followed by the addition of 150 $\mu$L Microscint™-CAT. The mix was allowed to incubate overnight prior to data acquisition.
Figure 2:
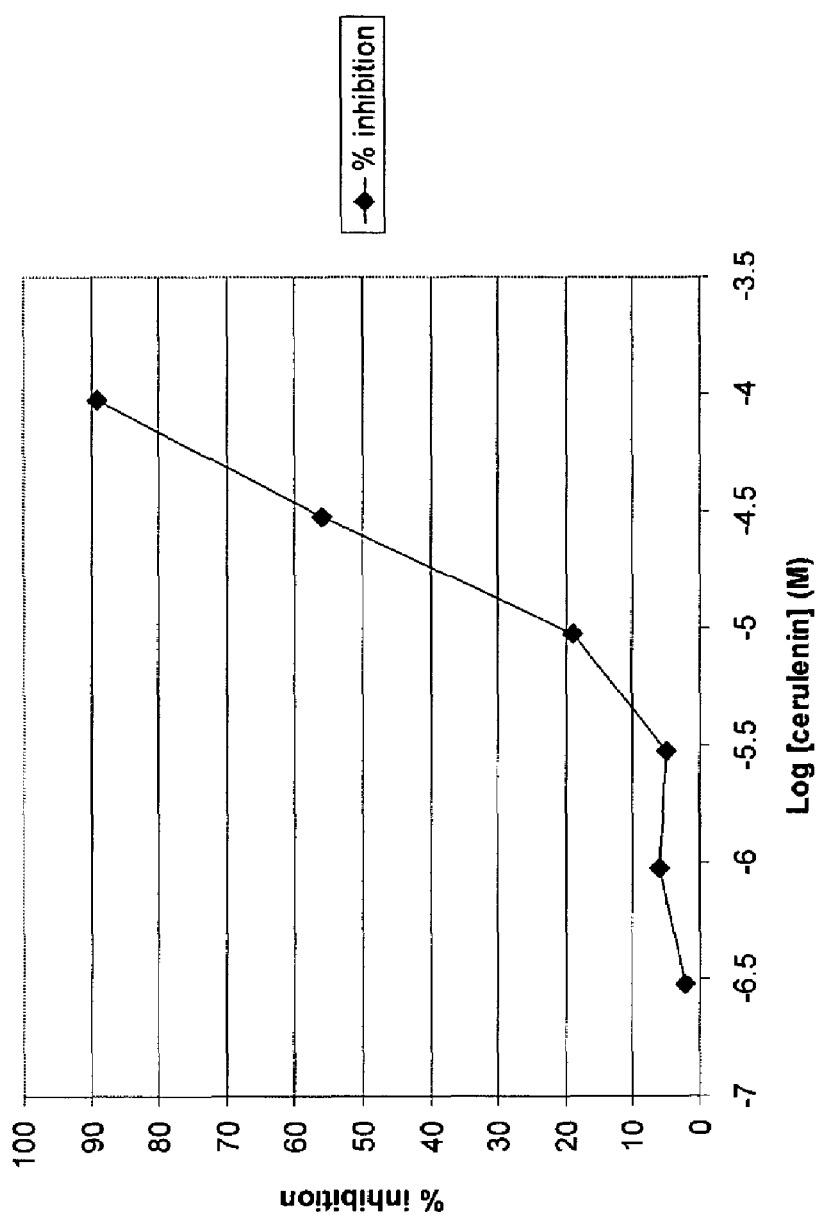
FIG. 2. Inhibition of FAS by cerulenin. FAS (35 ng) was incubated for 90 minutes with cerulenin under conditions described in FIG. 1.
Figure 3:
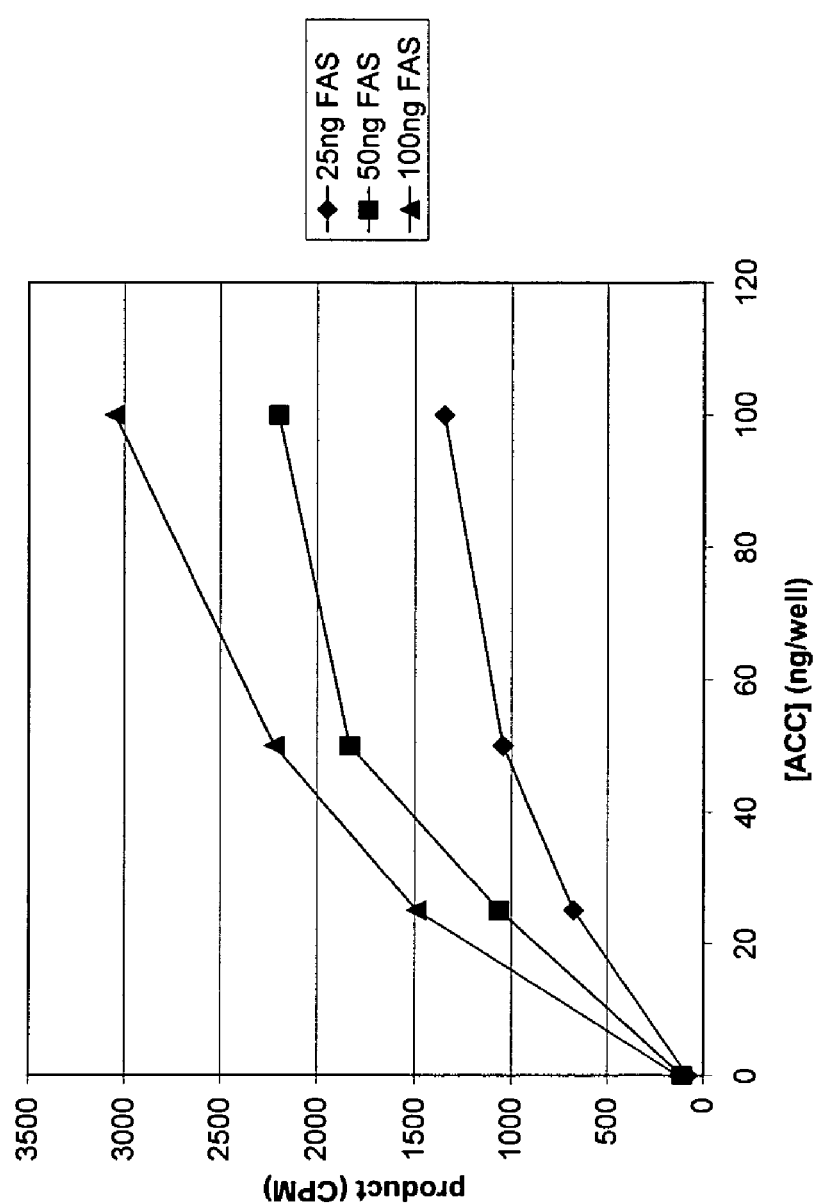
FIG. 3. Dose-dependence of acetyl CoA carboxylase (ACC)-produced product detected by FAS coupling and partitioning into the organic phase. ACC and FAS at varying concentrations were incubated for 75 minutes at room temperature with 4 mM ATP, 400 $\mu$M NADPH, and 16 $\mu$M acetyl-CoA (0.015 $\mu$Ci; [acetyl-1-$^{14}$C]-CoA) in a buffer containing 50 mM HEPES (pH 7.5), 20 mM NaHCO$_3$, 10 mM citric acid, 5 mM DTT, 10 mM MgCl$_2$, 1 mM EDTA, and 0.03% BSA in a total volume of 100 $\mu$L. The reaction was terminated by the addition 10 $\mu$L of 10 N acetic acid, followed by 150 $\mu$L Microscint™-CAT. The mix was allowed to incubate overnight prior to data acquisition.
Figure 4:
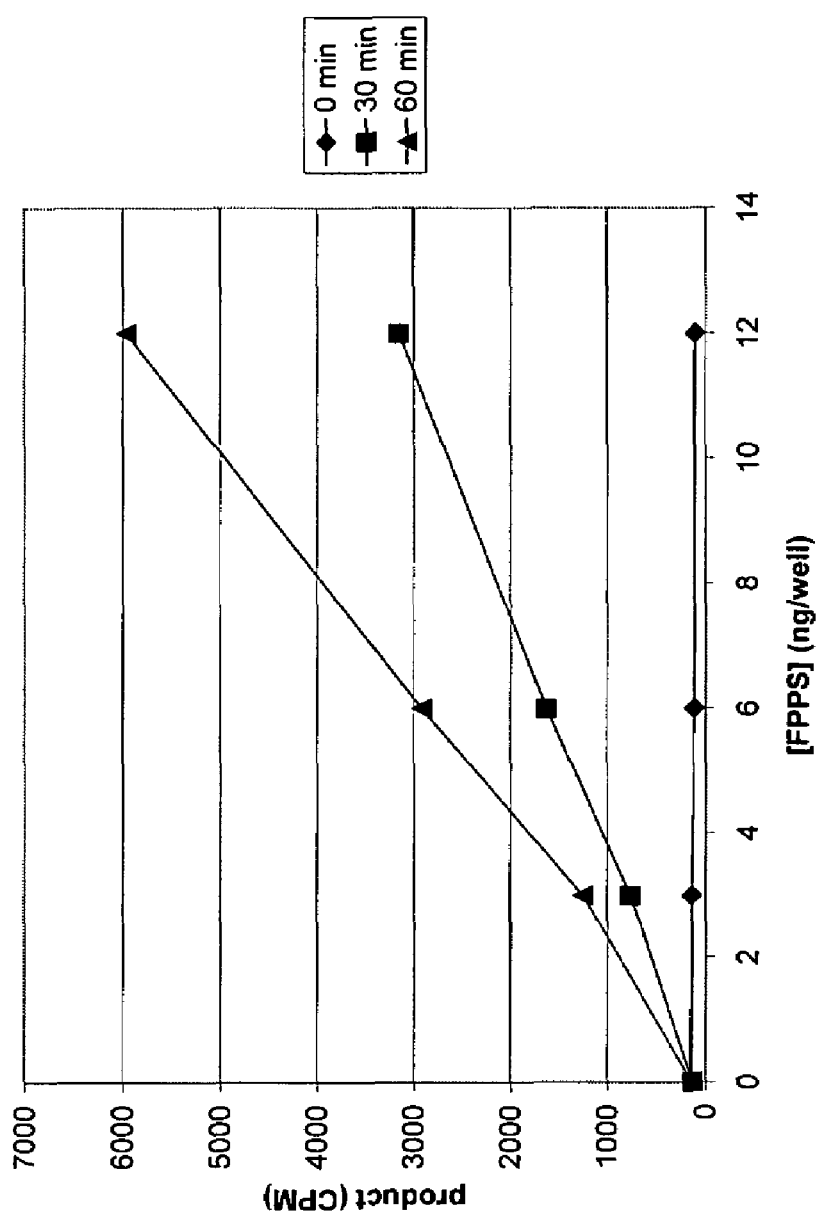
FIG. 4. Time course and protein dependence of farnesyl-diphosphate synthase (FPPS)-produced product partitioning into the organic phase. FPPS was incubated at varying concentrations and times at room temperature with 5 $\mu$M geranyl pyrophosphate (GPP) and 5 $\mu$M IPP (0.0125 $\mu$Ci; [1-$^{14}$C]isopentenyl pyrophosphate) in a buffer containing 25 mM HEPES (pH 7.5), 1 mM DTT, and 1 mM MgCl$_2$ in a total volume of 40 $\mu$L. The reaction was terminated by the addition of 10 $\mu$L of 5% phosphoric acid, followed by 50 $\mu$L Microscint™-CAT. The mix was allowed to incubate two hours prior to data acquisition.
Figure 5:
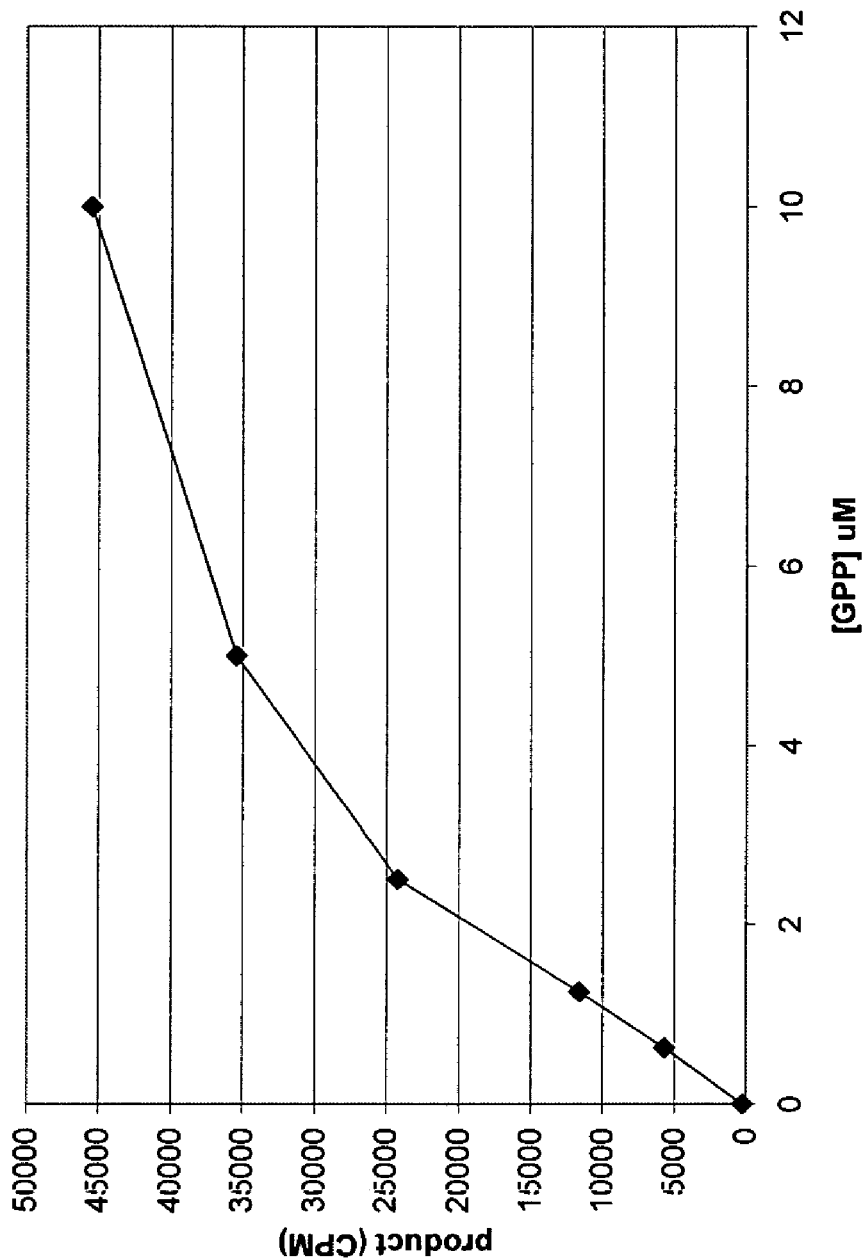
FIG. 5. FPPS product produced at a fixed concentration of isopentenyl pyrophosphate (IPP) (10 $\mu$M [1-$^{14}$C]isopentenyl pyrophosphate) and varying concentrations of GPP. The assay was performed as described in FIG. 4.
Figure 6:
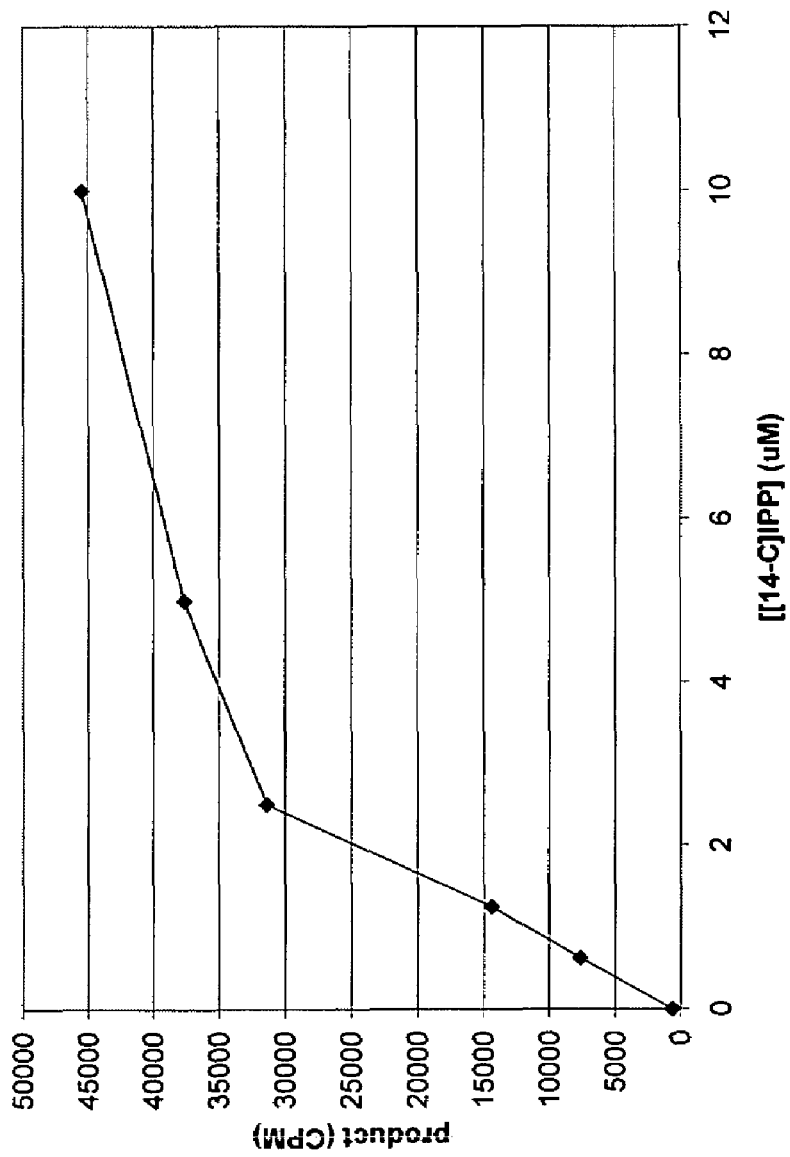
FIG. 6. FPPS product produced at a fixed concentration of GPP (10 $\mu$M) and varying concentrations of IPP (constant specific activity [1-$^{14}$C]isopentenyl pyrophosphate). The assay was performed as described in FIG. 4.
Figure 7:
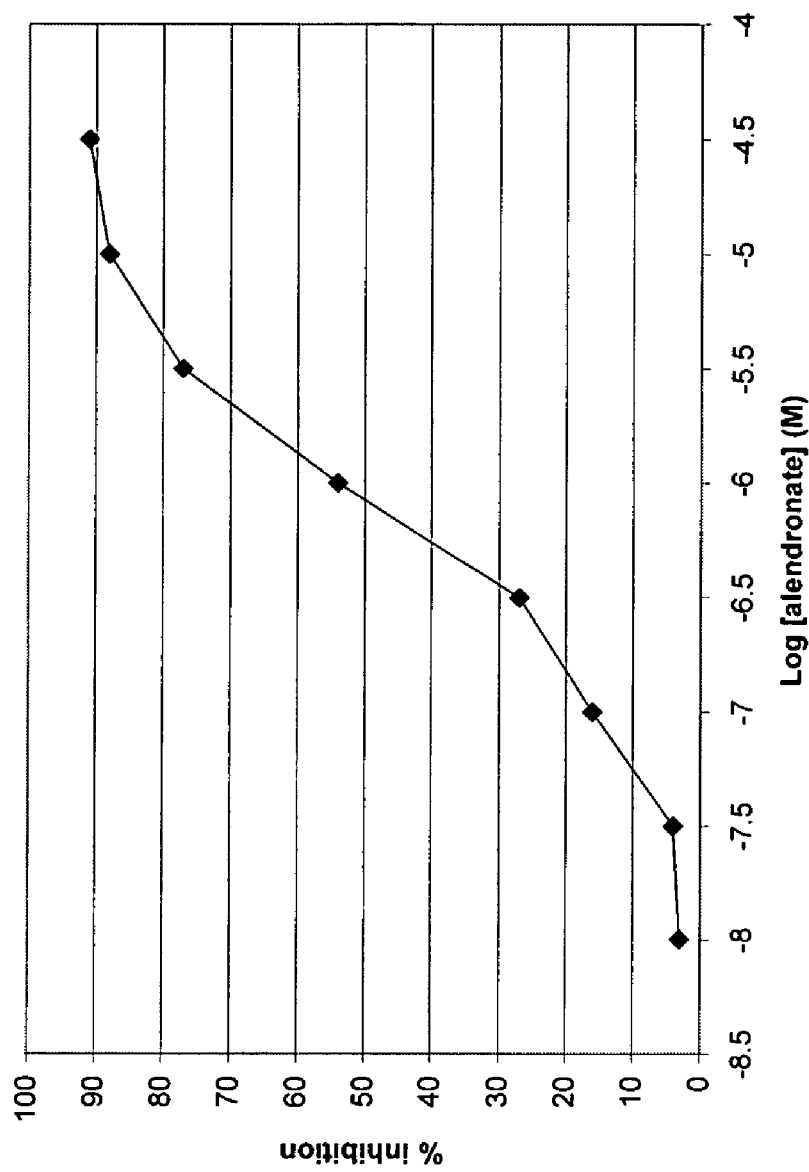
FIG. 7. Inhibition of FPPS by alendronate. FPPS (25 ng) was incubated for 2 hours with alendronate under conditions described in FIG. 4.
Figure 8:
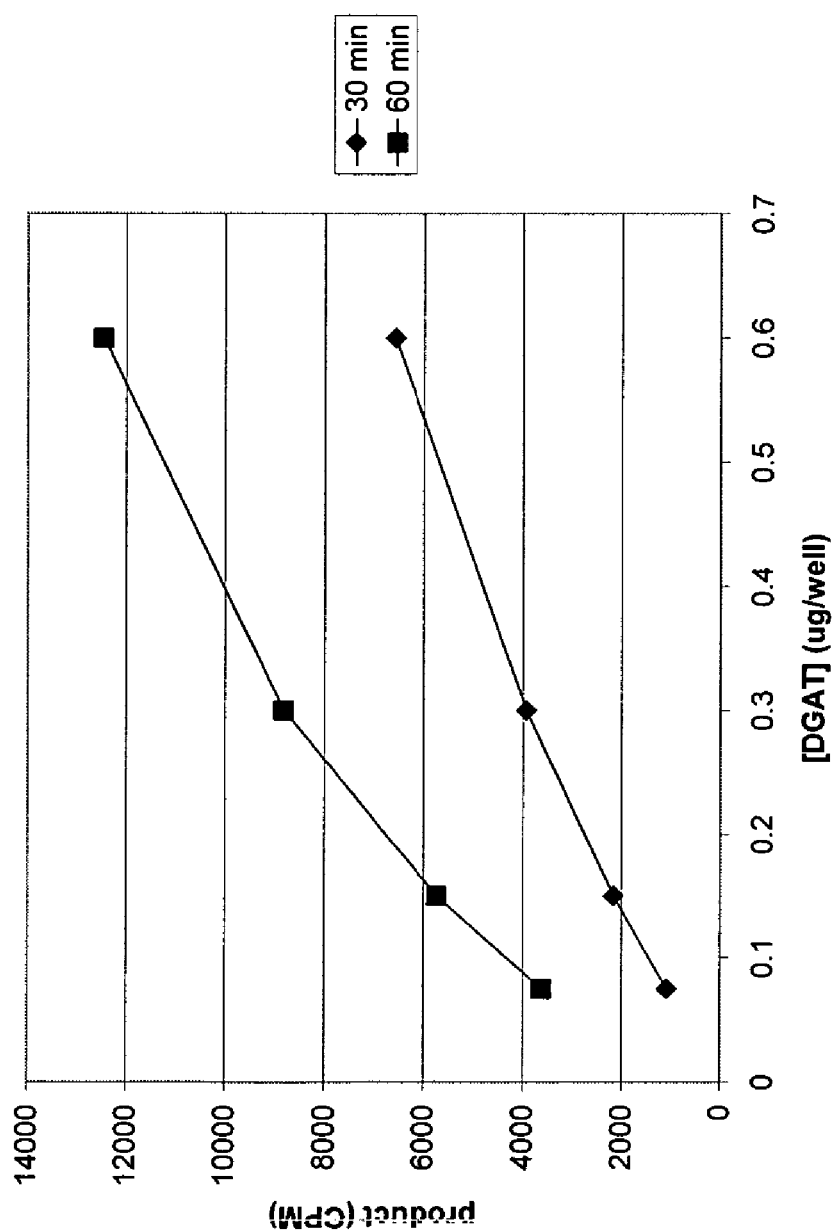
FIG. 8. Time course and protein dependence of diacylglycerol acetyltransferase (DGAT)-produced product partitioning into the organic phase. DGAT was incubated at varying concentrations and times at room temperature with 10 $\mu$M didecanoylglycerol and 10 $\mu$M decanoyl-CoA (0.025 $\mu$Ci; [1-$^{14}$C]decanoyl CoA) in a buffer containing 50 mM HEPES (pH 7.5), 1 mM $MgCl_2$, and 0.05% BSA in a total volume of 100 $\mu$L. The reaction was stopped by the addition of 20 $\mu$L of 1% phosphoric acid, followed by 150 $\mu$L Microscint™-CAT. The mix was allowed to incubate two hours prior to data acquisition.
Figure 9:
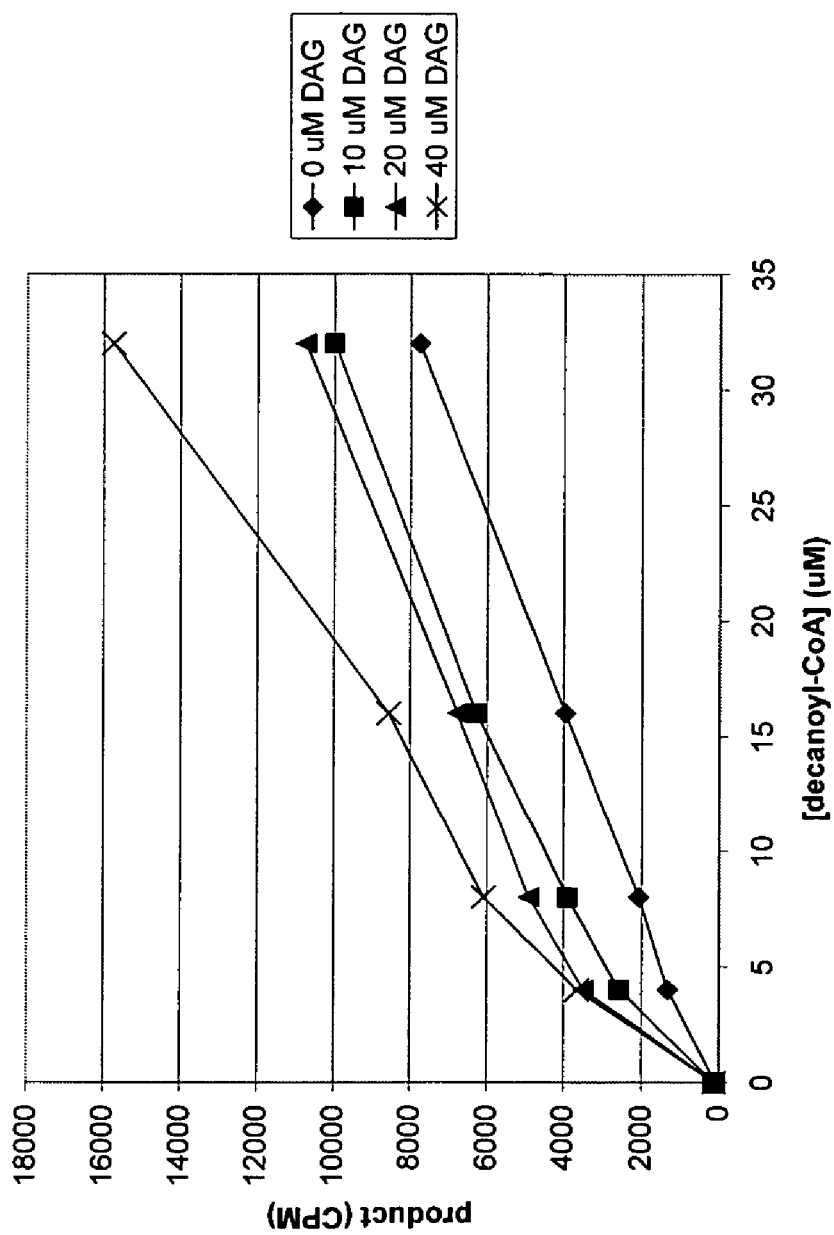
FIG. 9. DGAT activity as a function of decanoyl CoA and didecanoylglycerol concentration [substrates]. DGAT (250 ng) was incubated with varying concentrations of [1-$^{14}$C] decanoyl CoA and didecanoylglycerol for 45 minutes at room temperature under conditions described in FIG. 8.
Figure 10:
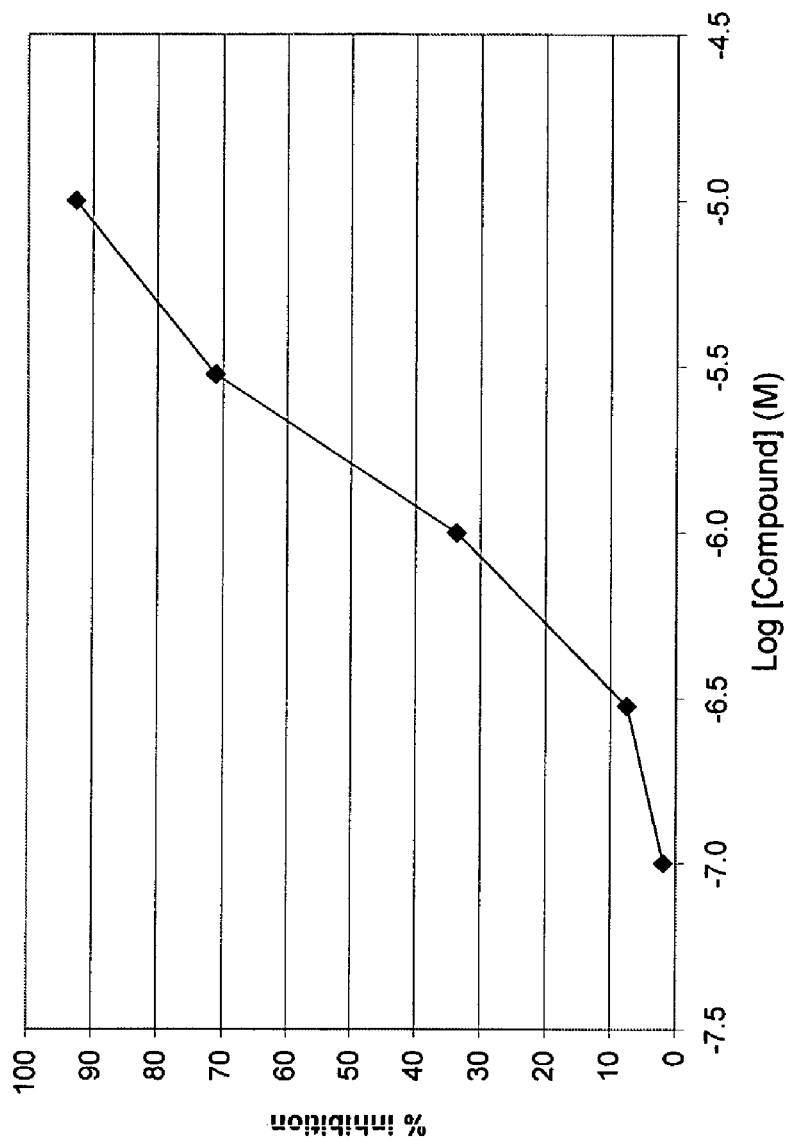
FIG. 10. Inhibition of DGAT by a test compound. DGAT (250 ng) was incubated for 1 hour with a test compound and substrates followed by work-up under conditions described in FIG. 8.
Figure 11:
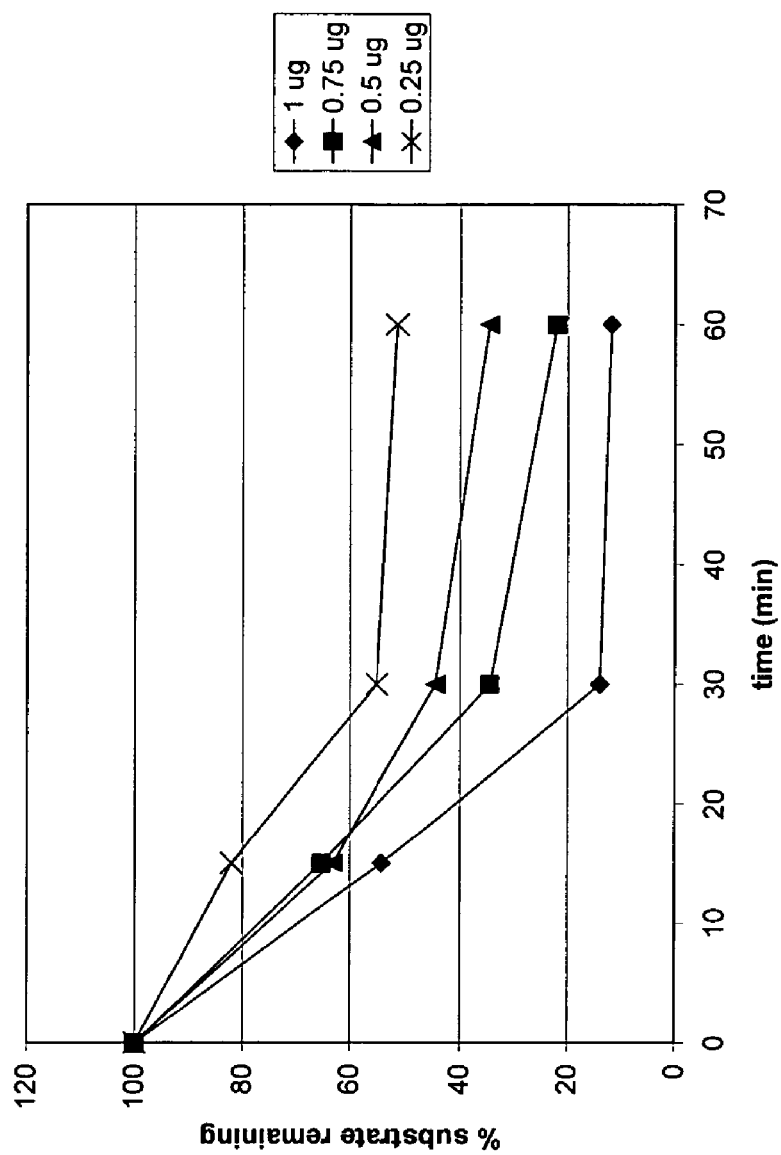
FIG. 11. Time course and protein dependence of PLC$\delta$-catalyzed product formation detected by loss of signal partitioning into the organic phase. PLC$\delta$ was incubated at varying concentrations and times at room temperature with 100 $\mu$M L-3-phosphatidyl inositol (0.02 $\mu$Ci L-3-phosphatidyl[2-$^3$H]inositol) in a buffer containing 75 mM MES (pH 6), 150 mM NaCl, 0.15 mM DTT, and 0.075% Triton X-100 in a total volume of 100 $\mu$L. The reaction was terminated by the addition of 10 $\mu$L of 5 N HCl, followed by 160 $\mu$L Aldrich LSM. The mix was allowed to incubate overnight prior to data.
Figure 12:
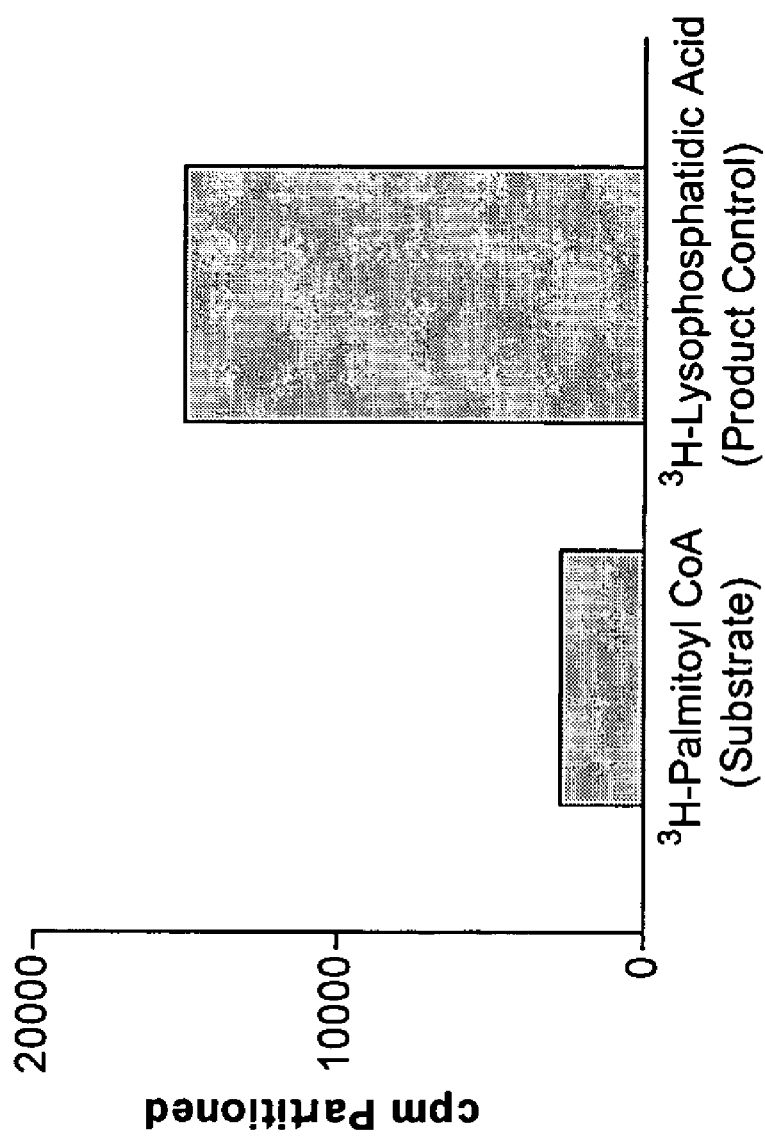
FIG. 12. Phase partition separation of palmitoyl-CoA from lysophosphatidic acid. A fixed amount of tritiated (0.1 $\mu$Ci) [$^3$H-9,10]palmitoyl-CoA and lysophosphatidic acid (1-oleoyl[$^3$H-9,10]glycerol 3-phosphate) were treated under standard partitioning conditions. This figure demonstrates that a phase partition assay detecting GPAT activity is feasible.
Figure 13:
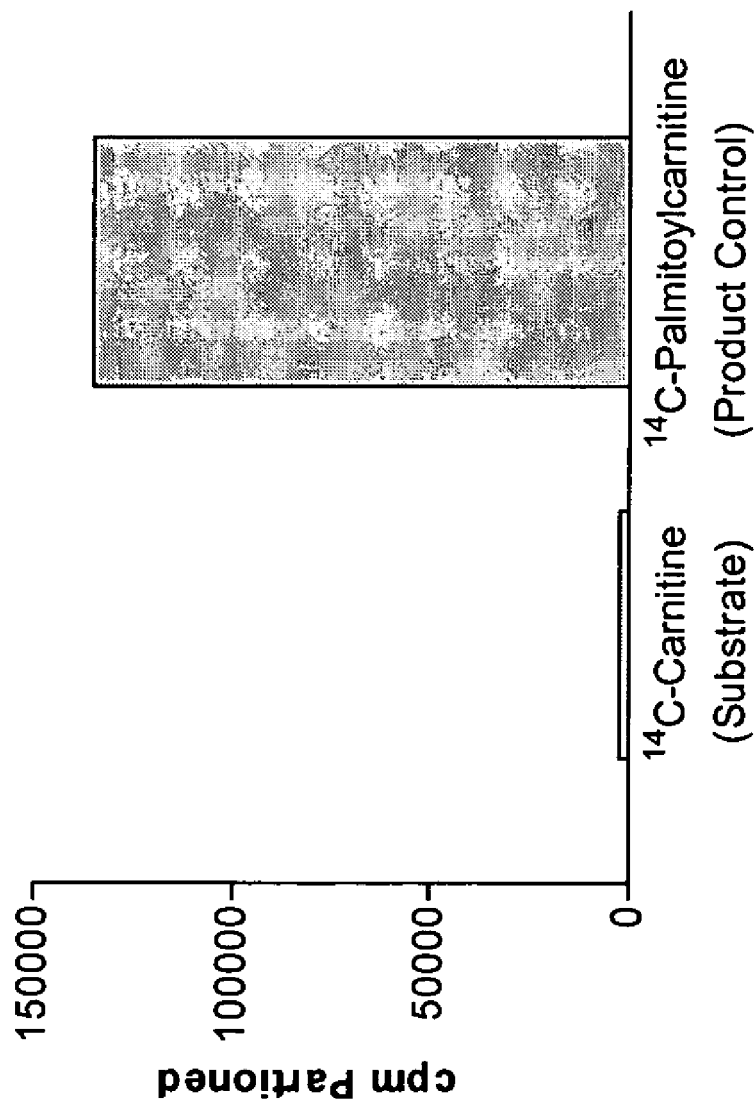
FIG. 13. Phase partition separation of carnitine from palmitoylcarnitine. A fixed amount of $^{14}$C-labeled (0.1 $\mu$Ci) [N-methyl-$^{14}$C]carnitine and [palmitoyl-1-$^{14}$C]palmitoylcarnitine were treated under standard partitioning conditions. This figure demonstrates that a phase partition assay detecting carnitine palmitoyltransferase activity is feasible.
Figure 14:
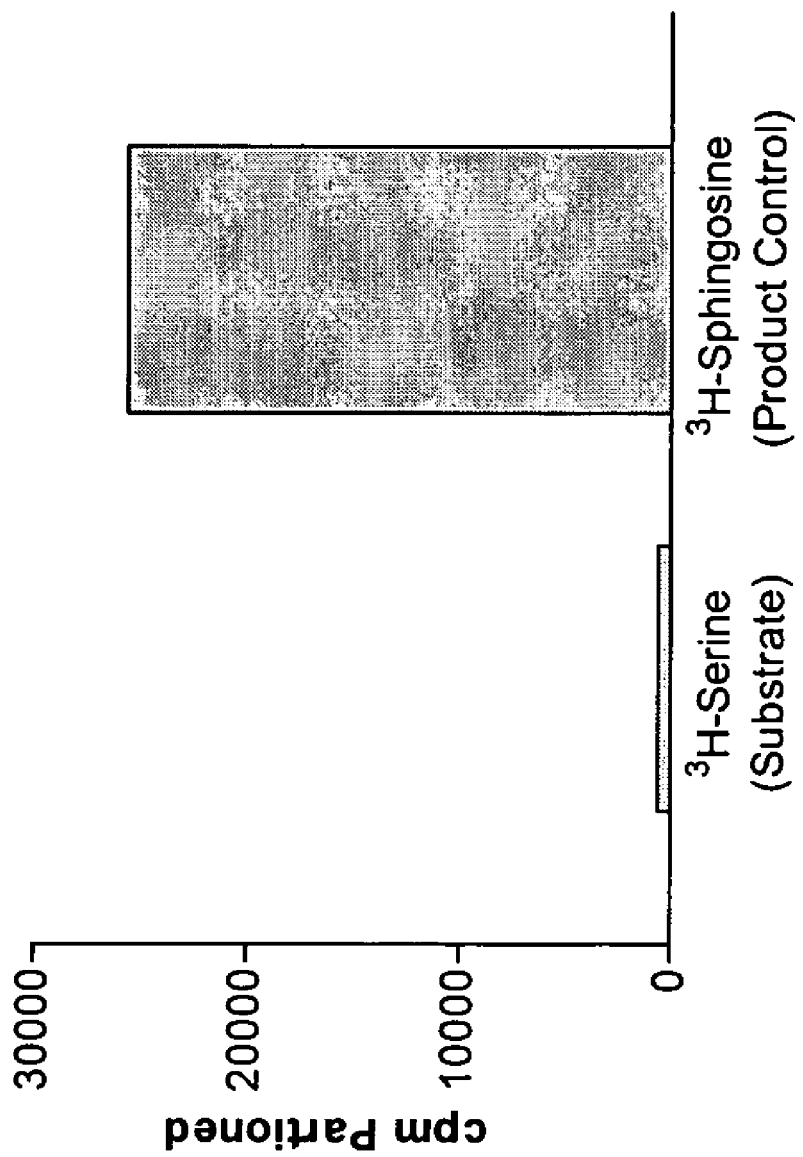
FIG. 14. Phase partition separation of serine from sphingosine. A fixed amount of tritiated (0.1 $\mu$Ci) [3-$^3$H]serine and D-erythro-[3-$^3$H]sphingosine were treated under standard partitioning conditions. This figure demonstrates that a phase partition assay detecting serine palmitoyltransferase activity is feasible.

The present invention provides methods for the quantitative measurement of enzyme activity in which a radiolabeled substrate and the product of the reaction are differentially partitioned into an aqueous phase and an immiscible scintillation fluid-containing organic phase. These methods exploit the fact that scintillations are only detected when the radionuclide is in the organic, scintillant-containing phase. Enzyme activity is assessed either by incorporation of a radiolabel-containing organic-soluble moiety into product molecules (gain of signal assay) or loss of a radiolabel-containing organic-soluble moiety from substrate molecules (loss of signal assay).

The two-phase system (organic/aqueous) is established by the addition of a specific phase-partition scintillation fluid (PPSF). The PPSF serves as a scintillation fluid, a phase partition agent, and a carrier/separator of an organic-soluble radiolabeled reaction substrate or product. Applying an empirically derived set of conditions typically enhances the separation of substrate from product whereby one species is effectively solubilized in the PPSF. For example, acidification of a reaction mixture containing a long chain fatty acid protonates the carboxyl group of the fatty acid, thereby making the fatty acid more soluble in the organic phase.

In situ partitioning (phase separation) of the radionuclide-containing organic/lipid phase from the aqueous phase occurs within individual wells of 96-well or 384-well (or greater than 96-well or 384-well) density microtiter plates without the requirement for multiple organic solvent extractions and aspirations. These methods are unique in the applicability to a large number of small volume samples that may be analyzed in a parallel (contemporaneous) manner using standard reagents and instrumentation common to an HTS laboratory within the pharmaceutical industry. These methods allow for a large library of compounds to be efficiently screened against enzymatic activities previously analyzed through traditional low throughput methods (e.g., HPLC or TLC). Therefore, these methods may be applied to discover molecules capable of modulation of a potential therapeutic target enzyme activity. That is, the invention provides methods which may be used to identify compounds which may act, for example, as regulators or modulators of enzyme activity such as agonists and antagonists, partial agonists, inverse agonists, activators, co-activators, and inhibitors.

There are two key considerations in utilizing these assay formats. First, an appropriate PPSF must be used with a compatible microtiter plate. The choice/pairing of scintillation fluid and microtiter plate is critical to the ability for the detection of disintegrations per minute (dpm). A disadvantage of many scintillation fluids is their tendency to penetrate the walls of the microtiter plate resulting in a compromise of the rigidity and integrity of the plate. The microtiter plate must be resistant to the penetration by the scintillation fluid for extended periods of time that are common to HTS (e.g., greater than 24 hours). Microscint™-CAT cocktail, MicroScint™-E cocktail (PerkinElmer, Boston, Mass.) or Liquid Scintillation Mixture (Aldrich, Milwaukee, Wis.; Aldrich LSM) meet the requirements of a PPFS, and are compatible with a solvent resistant class of microtiter plates (e.g., PicoPlate™, PerkinElmer, Boston, Mass.). Other scintillation fluids may act as PPSFs, but like ALDRICH LSM contain toluene or other organic based volatile components with higher permeation rates into standard plastic matrices. The increased volatility of these scintillation fluids also presents a health risk to the HTS analyst performing laboratory measurements.

The second consideration in establishing a phase partition assay is the proper choice of radiolabeled substrate(s) to ensure that the enzyme-catalyzed substrate-to-product conversion will allow for CPMs (counts per minute) and the associated substrate or product to partition into the desired phase. Target activity is assessed by incorporation of a radiolabel-containing organic-soluble moiety into product molecules or loss of a radiolabel-containing organic-soluble moiety from substrate molecules. An important caveat in performing this type of assay is ensuring that the choice of radiolabeled substrate and product meet the following requirements. First, the regiochemistry of the enzyme-catalyzed reaction must be compatible with the location of the radiolabel in the substrate, so that radiolabel is not released into the media upon enzyme reaction. For example, ornithine radiolabeled at C-1 with 14-carbon cannot be used to monitor the decarboxylation of ornithine catalyzed by ornithine decarboxylase due to the volatile product [$^{14}$C] carbon dioxide. Similarly, the release of tritium in the form of tritiated water is unacceptable. Second, the enzymatic reaction must alter the physicochemical properties of the substrate to enable differential partitioning of the product into the opposite phase. The combination of a PPSF and an organic resistant microtiter plate and the appropriate choice of radiolabeled substrate(s) (and consideration of products) allows for enzymatic activity to be assessed via a gain of radiosignal or loss of radiosignal measurement. Both assay types are performed with minimal addition steps in the primary assay plate. Gain of signal assays includes, for example, Fatty Acid Synthase (FAS); Acetyl CoA Carboxylase (ACC); Diacylglycerol Acetyltransferase (DGAT); Farnesyl Diphosphate (FPP) Synthase; Glycerol-3-Phosphate O-Acyltransferase (GPAT); Carnitine O-palmitoyltransferase 1 (CPT1); and Serine C-Palmitoyltransferase (SPT). Loss of signal assays includes, for example, Phospholipase C gamma (PLCδ).

Fatty Acid Synthase

FAS catalyzes the formation of long chain fatty acids from acetyl-CoA, malonyl-CoA, and NADPH. This multifunctional protein has 7 catalytic activities and an acyl carrier protein. It is required for de novo fatty acid synthesis and energy balance.

Net Reaction:

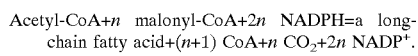
Acetyl-CoA+$n$ malonyl-CoA+$2n$ NADPH=a long-chain fatty acid+($n$+1) CoA+$n$ CO$_2$+$2n$ NADP$^+$.

Catalytic Activity (1):

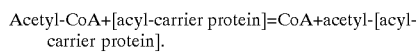
Acetyl-CoA+[acyl-carrier protein]=CoA+acetyl-[acyl-carrier protein].

Catalytic Activity (2):

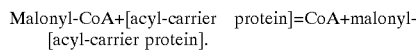
Malonyl-CoA+[acyl-carrier protein]=CoA+malonyl-[acyl-carrier protein].

Catalytic Activity (3):

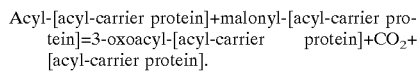
Acyl-[acyl-carrier protein]+malonyl-[acyl-carrier protein]=3-oxoacyl-[acyl-carrier protein]+CO$_2$+[acyl-carrier protein].

Catalytic Activity (4):

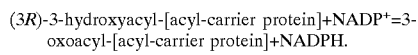
(3$R$)-3-hydroxyacyl-[acyl-carrier protein]+NADP$^+$=3-oxoacyl-[acyl-carrier protein]+NADPH.

Catalytic Activity (5):

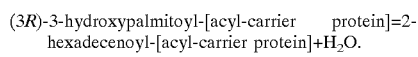
(3$R$)-3-hydroxypalmitoyl-[acyl-carrier protein]=2-hexadecenoyl-[acyl-carrier protein]+H$_2$O.

Catalytic Activity (6):

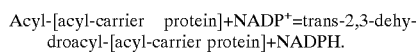
Acyl-[acyl-carrier protein]+NADP$^+$=trans-2,3-dehydroacyl-[acyl-carrier protein]+NADPH.

Catalytic Activity (7):

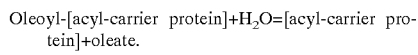
Oleoyl-[acyl-carrier protein]+H$_2$O=[acyl-carrier protein]+oleate.

This method of the present invention permits radiometric detection of FAS activity via a gain of signal assay using [2-$^{14}$C]malonyl CoA as the radiolabel and partitioning of the radioactive products ($^{14}$C-labeled oleic acid and palmitic acid) into the PPSF (Microscint™-E), following acidification and addition of PPSF to the reaction mixture.

A typical 96-well density reaction is partitioned in the following manner: an enzyme assay inhibitor test mix (100 μL) containing enzyme, substrates, test compounds, and buffer components is incubated at room temperature to generate the fatty acid products. The enzymatic reaction is stopped by the addition of 20 μL of 2N HCl, followed by addition of 150 μL Microscint™-E. Partitioning does not require a specific mixing step, but does require several hours for establishment and is stable for 24 hours. The radioactive substrate, [2-$^{14}$C]malonyl CoA, does not partition into the organic phase under these conditions. This is verified using [2-$^{14}$C]malonyl CoA under standard assay and partition conditions, but substituting-heat inactivated FAS for viable FAS. Enzyme activity is proportional to the radioactivity in the organic phase as determined by liquid scintillation counting. The amount of radioactivity detected in the PPSF is dependent upon the amount of FAS in the well and the amount of time the enzymatic reaction is allowed to proceed, that is, CPMs are dose-dependent with respect to reaction time and concentration of FAS. Kinetic parameters obtained by this method are consistent with the literature values by standard methods. The effectiveness of acidification and the PPSF in partitioning long chain fatty acids into the PPSF may be verified using a known amount of authentic radiolabeled [1-$^{14}$C]palmitic acid. The theoretical signal to background of the assay is established by comparing CPMs in the PPSF using radiolabeled substrate and product.

This method of the present invention is more sensitive than spectrophotometric assays which monitor consumption of co-substrate NADPH (loss of absorbance at 340 nm) rather than production of fatty acid product (see, e.g., Martin, et al., J. Biol. Chem. 236:663–668, 1961). Furthermore, this method of the present invention is a single pot method (a single reaction vessel, e.g., centrifuge tube or a single well of a multiple well plate) and thus, avoids mixing steps, multiple transfers, and extractions typical of traditional methods (see, e.g., Arslanian, et al., Methods Enzymol. 35:59–65, 1975; Singh, et al., J. Biol. Chem. 259: 3605–3611, 1984). This reduces the time required for analysis several fold. In addition, the method of the present invention provides that the enzymatic reaction and analysis may be performed utilizing 96-well or 384-well density plates in volumes from 100 μL to 270 μL (i.e., 384-well density and 96-well density, respectively). Traditional assays are generally performed in large volumes (e.g., a typical primary assay volume of 0.5 mL) followed by a base-catalyzed hydrolysis step, boiling step, acidification step, and multiple extractions into pentane.

Acetyl-CoA Carboxylase 1

ACC catalyzes the rate-limiting reaction in the biogenesis of long-chain fatty acids. This protein uses biotin as a cofactor, and has three functions: biotin carboxyl carrier protein, biotin carboxylase, and carboxyltransferase, with two discrete activities:

Catalytic Activity (1):

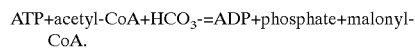
ATP+acetyl-CoA+HCO$_3$-=ADP+phosphate+malonyl-CoA.

Catalytic Activity (2):

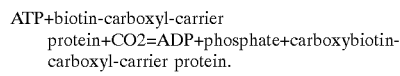
ATP+biotin-carboxyl-carrier protein+CO2=ADP+phosphate+carboxybiotin-carboxyl-carrier protein.

This method of the present invention permits radiometric detection of ACC activity via a gain of signal assay using the

[2-$^{14}$C]malonyl-CoA product of the reaction between NaHCO$_3$ and [1-$^{14}$C]acetyl-CoA catalyzed by ACC, as a substrate for FAS. This method permits radiometric detection of ACC activity by partitioning the radioactive products of the ACC-FAS coupled assay ($^{14}$C-radiolabled oleic acid and palmitic acid) into the PPSF (Microscint™-E) following acidification of the reaction mixture.

A typical 96-well density reaction is partitioned in the following manner: 100 μL enzyme assay inhibitor test mix containing enzyme (ACC and FAS), substrates, test compounds, and buffer components is incubated at room temperature to generate the fatty acid products. The enzymatic reaction is stopped by the addition of 20 μL of 2N HCl, followed by addition of 150 μL Microscint™-E. Partitioning does not require a specific mixing step, but does require several hours for establishment and is stable for 24 hours. Neither the radioactive substrate [1-$^{14}$C]acetyl-CoA nor the product of the ACC reaction [2-$^{14}$C]malonyl-CoA partitions into the organic phase. This is verified using a mixture of [1-$^{14}$C]acetyl-CoA and [2-$^{14}$C]malonyl CoA under standard assay conditions and partition conditions, but substituting heat-inactivated ACC and FAS for viable ACC and FAS. Enzyme activity is proportional to the radioactivity in the organic phase as determined by liquid scintillation counting. The amount of radioactivity detected in the PPSF is dependent upon the amount of FAS in the well and the amount of time the enzymatic reaction is allowed to proceed, that is, CPMs are dose-dependent with respect to reaction time and concentration of ACC. Kinetic parameters obtained by this method are consistent with the literature values by standard methods. The effectiveness of acidification and the PPSF in partitioning long chain fatty acids into the PPSF may be assessed using a known amount of authentic radiolabeled palmitic acid. The theoretical signal to background of the assay may be established by comparing CPMs in the PPSF using equimolar amounts and equal amounts of radioactivity of radiolabeled substrate and product.

This method of the present invention provides a means to measure a complete catalytic cycle of ACC, and is more sensitive than a spectrophotometric assay that measures the partial reaction of ATP-dependent biotin (Levert, et al., Biochemistry, 39:4122–4128, 2000). The rate of ATP hydrolysis by biotin carboxylase was measured spectrophotometrically at 340 nm by coupling the production of ADP to pyruvate kinase and lactate dehydrogenase.

This method of the present invention method also measures the biologically relevant forward reaction catalyzed by ACC (malonyl-CoA production), is a direct in-line coupling reaction, and is more sensitive than the spectrophotometric assay that monitors the ACC-catalyzed decarboxylation of malonyl-CoA (Winder, et al., J. Appl. Physiol. 88:2219–2226, 2000). This spectrophotometric assay condenses the acetyl-CoA produced in the ACC reaction with oxaloacetic acid produced by the action of malate dehydrogenase on malate and NAD to produce citrate in a citrate synthase catalyzed reaction. NADH production is measured as increase in absorbance at 340 nm.

Furthermore, this method of the present invention is safer and less labor intensive as compared to other radiolabeled assays. For example, the method of Herbert and co-workers measures the production of [3-$^{14}$C]malonyl-CoA from NaH14CO$_3$ and acetyl-CoA (Herbert, et al., Biochem. J. 318:997–1006, 1996). Their method requires transfer of the product to a separate vial, acid-catalyzed elimination of remaining NaH$^{14}$CO$_3$ as $^{14}$CO$_2$, drying, and re-dissolution of product for liquid scintillation counting. The method of Wada and co-workers measures fatty acids produced from the action of mitochondrial enzymes on [1-$^{14}$C]acetyl-CoA (Wada, et al., Proc. Natl. Acad. Sci. USA 94:1591–1596, 1997). Their method uses endogenous ACC and FAS, thereby producing oleic and palmitic acid. However, this method also involves acid-catalyzed formation of isopropyl fatty acid esters, extraction into hexane, and analysis by thin layer chromatography (TLC).

In addition, this method of the present invention provides that the enzymatic reaction and analysis may be performed in the well of a 96-well or 384-well density plate in volumes from 100 μL to 270 μL (i.e., 384-well density and 96-well density, respectively). Traditional radioactive assays are performed in tubes in large volumes (e.g., a typical primary assay volume of 0.5 mL) followed by multiple manipulation steps.

Farnesyl-diphosphate Synthase
    Catalytic Activity

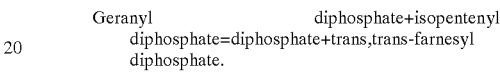

Geranyl diphosphate+isopentenyl diphosphate=diphosphate+trans,trans-farnesyl diphosphate.

This method of the present invention permits radiometric detection of FPP synthetase activity by partitioning the radioactive product of the reaction between [1-$^{14}$C]isopentenyl pyrophosphate and geranyl diphosphate, [1-$^{14}$C]trans, trans-farnesyl diphosphate (FPP), into the PPSF following acidification of the reaction mixture. Acid treatment of FPP yields a mixture of [1-$^{14}$C]farnesol (depyrophosphorylated alcohol product) and [1-$^{14}$C]nerolidol (3,7,11-trimethyl-1,6, 10-dodecatrien-3-ol; alcohol product from depyrphosphorylation followed by carbocation rearrangement; Holloway, et al., Biochem. J. 104:57–70, 1967). Both nerolidol and farnesol are organic soluble. The radioactive substrate [1-$^{14}$C]isopentyl pyrophosphate is acid stable and does not partition into the organic phase. The separation of unconsumed substrate (and associated DPMs) from the product (incorporating DPMs from substrate) is achieved by a combination of acidification of the FPP synthetase reaction mixture which serves to transform the organic non-miscible (aqueous miscible) product into organic miscible allylic alcohol products, followed by addition of the PPSF.

A typical 384-well density reaction is partitioned with the following proportion of reagents: 40 μL enzyme assay inhibitor test mix containing FPP synthetase, substrates, test compounds, and buffer components is incubated at room temperature to generate farnesyl diphosphate. The enzymatic reaction is terminated by the addition of 10 μL of 5% phosphoric acid followed by 50 μL Microscint™-E. Partitioning does not require a specific mixing step, but does require several hours for establishment and is stable for 24 hours. [1-$^{14}$C]isopentenyl pyrophosphate is stable under these conditions and does not partition into the organic phase. Acid stability of this species is documented in the literature, and control reactions using heat-inactivated FPP synthetase in place of viable FPP synthetase verify that substrate does not partition into the organic phase under standard assay conditions. Enzyme activity is proportional to the radioactivity in the organic phase as determined by liquid scintillation counting (LSC). This radioactivity corresponds to products of acid treatment of the enzyme reaction, farnesol and nerolidol, as determined by LSC of authentic [1,2-$^{14}$C]trans, trans farnesol. The amount of radioactivity detected in the PPSF is dependent on the amount of FPPS in the well and the amount of time the enzymatic reaction is allowed to proceed, that is, CPMs are dose-dependent with respect to time and concentration of FPPS. Kinetic parameters obtained by this method are consistent with literature methods obtained by standard methods. The theoretical signal to background of the assay is established by comparing CPMs in the PPSF using equimolar amounts and equal amounts of radioactivity of radiolabeled substrate and product. Because phase separation is achieved within the same well of the microtiter plate where the enzymatic incubation occurred, quantitative analysis and processing of samples can be achieved in a high throughput manner.

The method of the present invention reduces the original large scale reaction (1 mL) and multistep analysis (acidification; neutralization; repeated extraction into petroleum ether) of Holloway and Popjak to a single pot reaction, and does not require mixing or removal/separation of phases (Holloway, et al., Biochem. J. 104:57–70, 1967). This reduces the time for analysis several fold.

The method of the present invention provides that the enzymatic reaction and analysis may be performed in the well of a 96-well or 384-well density plate in volumes from 100 μL to 270 μL (i.e., 384-well density and 96-well density, respectively). Traditional assays are performed in tubes or separatory funnels.

Diacylglycerol O-acyltransferase 1

DGAT catalyzes the terminal and only committed step in triacylglycerol synthesis by using diacylglycerol and fatty acyl CoA as substrates.

Catalytic Activity:

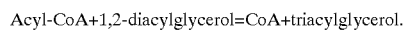

Acyl-CoA+1,2-diacylglycerol=CoA+triacylglycerol.

This method of the present invention permits radiometric detection of DGAT activity via a gain of signal assay by partitioning the radioactive product tri-decanoyl glycerol formed from the DGAT-catalyzed condensation of di-decanoyl glycerol with [1-$^{14}$C]decanoyl-CoA into the PPSF (Microscint™-E).

A typical 96-well density reaction is partitioned in the following manner: 100 μL enzyme assay inhibitor test mix containing DGAT, substrates, test compounds, and buffer components is incubated at room temperature to generate triacylglycerol product. The enzymatic reaction is terminated by the addition of 20 μL of 1% phosphoric acid followed by addition of 150 μL Microscint™-E. Partitioning does not require a specific mixing step, but does require several hours for establishment and is stable for 24 hours. The radioactive substrate [1-$^{14}$C]decanoyl-CoA does not partition into the organic phase. This is verified using [1-$^{14}$C]decanoyl-CoA under standard assay conditions and partition conditions but substituting heat-inactivated DGAT for viable DGAT. Enzyme activity is proportional to the radioactivity in the organic phase as determined by liquid scintillation counting. The amount of radioactivity detected in the PPSF is dependent upon the amount of DGAT in the well and the amount of time the enzymatic reaction is allowed to proceed, that is, CPMs are dose-dependent with respect to reaction time and concentration of DGAT. Kinetic parameters obtained by this method are consistent with the literature values by standard methods. The effectiveness of acidification and the PPSF in partitioning tri-decanoyl glycerol into the PPSF is verified using a known amount of [hexadecanoyl1-$^{14}$C]tri-hexadecanoyl glycerol. This is used as a substitute for tri-decanoyl glycerol which is not commercially available, and it should have similar partitioning characteristics. The theoretical signal to background of the assay is established by comparing CPMs in the PPSF using equimolar amounts and equal amounts of radiolabeled substrate and product (substitution of [hexadecanoyl1-$^{14}$C]tri-hexadecanoyl glycerol for tri-decanoyl glycerol).

Since phase separation is achieved within the same well of the microtiter plate where the enzymatic incubation occurred, quantitative analysis and processing of samples may be achieved in a high throughput manner. The application of this method is not limited to di-decanoyl glycerol and decanoyl-CoA; a variety of fatty acid diacylglycerols and fatty acid-CoAs may be used.

The method of the present invention reduces the traditional analysis of multiple transfers and extractions to a single pot reaction and does not require mixing or removal/separation of phases. Traditional methods involve performing assays in individual tubes, extraction of product into a mixed aqueous:organic phase system, vortexing, aqueous washing, and thin layer chromatography. The method of the present invention reduces the time for analysis several fold.

The method of the present invention provides that the enzymatic reaction and analysis may be performed in the well of a 96-well or 384-well density plate in volumes from 100 μL to 270 μL (384-well density and 96-well density, respectively). Traditional assays are performed in tubes in large volumes (e.g., a typical primary assay volume of 0.2 mL) followed by an organic phase quench step, multiple extractions into heptane with subsequent wash steps of the resulting organic phase (see, e.g., Coleman, et al., J. Biol. Chem. 251:4537–4543, 1976; Andersson, et al., J. Lipid Res. 35:535–545, 1994). Enzyme activity is quantitated by thin layer chromatography.

1-Phosphatidylinositol-4,5-bisphosphate phosphodiesterase gamma-1

PLCδ-1 is a major substrate for the heparin-binding growth factor 1 (Acidic Fibroblast Growth Factor)-activated tyrosine kinase.

Catalytic Activity:

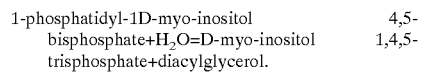

1-phosphatidyl-1D-myo-inositol 4,5-bisphosphate+H$_2$O=D-myo-inositol 1,4,5-trisphosphate+diacylglycerol.

This method of the present invention permits radiometric measurement of PLCδ-1 activity via a loss of signal assay by partitioning the radioactive product [inositol-2-$^3$H]1-phosphate into the aqueous phase and unhydrolyzed substrate L-3-phosphatidyl[2-$^3$H]inositol ([$^3$H]PI) into the PPSF (ALDRICH LSM). The natural substrate, inositol 4,5-bisphosphate, and the product of the PLCδ-catalyzed reaction, inositol 1,4,5-triphosphate, are both soluble in the aqueous phase, and a loss of signal assay is not possible. This substitution of phosphatidylinositol for phosphatidylinositol 4,5-phosphate as a substrate for PLCδ has been reported (Rhee, et al., Methods Enzymol. 197:502–511, 1991).

A typical 96-well density reaction is partitioned in the following manner: 100 μL enzyme assay inhibitor test mix containing PLCδ, substrates, test compounds, and buffer components is incubated at room temperature to generate inositol phosphate product. The enzymatic reaction is terminated by the addition of 10 μL of 5N HCl, followed by addition of 160 μL ALDRICH LSM. Partitioning does not require a specific mixing step, but does require eight hours for establishment, and is stable for 24 hours. The radioactive substrate readily partitions into the organic phase. This is verified using L-3-phosphatidyl[2-$^3$H]inositol ([$^3$H]PI under standard assay conditions and partition conditions, but substituting heat-inactivated PLCδ for viable PLCδ. Enzyme activity is inversely proportional to the radioactivity in the organic phase as determined by liquid scintillation counting. The amount of radioactivity detected in the PPSF is inversely dependent upon the amount of PLCδ in the well and the amount of time the enzymatic reaction is allowed to proceed, that is, CPMs are inversely dose-dependent with respect to reaction time and concentration of PLCδ. Kinetic parameters obtained by this method are consistent with the literature values obtained by standard methods. The effectiveness of acidification and the PPSF in partitioning phosphatidyl [2-$^3$H]inositol into the PPSF is assessed using a known amount of phosphatidyl [2-$^3$H]inositol. The theoretical signal to background of the assay is established by comparing CPMs in the PPSF using equimolar amounts and equal amounts of radiolabeled substrate phosphatidyl [2-$^3$H] inositol and product inositol phosphate.

Since phase separation is achieved within the same well of the microtiter plate where the enzymatic incubation occurred, quantitative analysis and processing of samples can be achieved in a high throughput manner.

Enzyme activity is proportional to the radioactivity in the organic phase as determined by liquid scintillation counting. For this purpose, ALDRICH LSM is superior to Microscint™-E, Instafluor (Packard BioScience, Groningen, The Netherlands) or Opto-fluor-O (Packard BioScience, Groningen, The Netherlands). Kinetic parameters and inhibitor effects obtained by this method are consistent with the literature values by standard methods.

The method of the present invention reduces the traditional analysis of multiple transfer and extraction steps to a single pot reaction and does not require mixing or removal/separation of phases. This reduces the time for analysis several fold. For example, Sekiya and coworkers terminate the primary enzymatic reaction (100 μL) with trichloroacetic acid (200 μL) and 10% bovine serum albumin (100 μL) followed by centrifugation. An aliquot of the aqueous phase is then removed for quantitation of inositol phosphate product by liquid scintillation counting (Sekiya, et al., J. Biol. Chem. 274:13900–13907, 1999). Thus, a single pot reaction reduces the time for analysis several fold.

Glycerol-3-phosphate O-acyltransferase

Glycerol-3-phosphate O-acyltransferase (GPAT) catalyzes the first committed step of glycerol lipid biosynthesis: the esterification of glycerol-3-phosphate in the sn-1 position with a fatty acyl-CoA to form 1-acylglycerol-3-phosphate (lysophosphatidic acid). There are microsomal and mitochondrial (mt) isozymes of this protein. In most tissues, mtGPAT contributes 10% of the total GPAT activity, however in liver, mtGPAT contributes 30 to 50% of the total activity. Microsomal GPAT esterifies both saturated and unsaturated fatty acyl-CoAs equally well, however mtGPAT has a substrate preference for palmitoyl-CoA.

Catalytic Activity

Acyl-CoA+sn-glycerol-3-phosphate=CoA+1-acyl-sn-glycerol 3-phosphate

This method of the present invention permits radiometric detection of GPAT activity via a gain of signal assay partitioning the 1-palmitoyl[$^3$H-9,10]glycerol 3-phosphate product of the reaction between [$^3$H-9,10]palmitoyl-CoA and sn-glycerol-3-phosphate into the PPSF (Microscint™-E).

Because authentic GPAT was not available for assay development, radiolabeled substrate and product, ([$^3$H-9,10] palmitoyl-CoA and lysophosphatidic (1-oleoyl[$^3$H-9,10] glycerol 3-phosphate) respectively, were used as controls. A typical 96-well density reaction is partitioned in the following manner: 100 μL assay inhibitor test mix containing substrates or products and buffer components is incubated at room temperature for 1 hour. This incubation is followed by two subsequent additions of 5 μL of 5% phosphoric acid and 120 μL Microscint™-E. Partitioning does not require a specific mixing step, but does require several hours for establishment and is stable for 24 hours. The radioactive [$^3$H-9,10]palmitoyl-CoA partitions poorly into the organic phase. The amount of radioactivity detected in the PPSF is dependent upon the amount of (1-oleoyl[$^3$H-9,10]glycerol 3-phosphate) in the well. Because 1-palmitoyl[$^3$H-9,10] glycerol 3-phosphate is not commercially available, 1-oleoyl [$^3$H-9,10]glycerol 3-phosphate is used as a substitute. 1-Oleoyl[$^3$H-9,10]should have similar partitioning characteristics as 1-palmitoyl[$^3$H-9,10]glycerol 3-phosphate. The theoretical signal to background of the assay is established by comparing CPMs in the PPSF using equimolar amounts and equal amounts of radiolabeled substrate and product (substitution of 1-oleoyl[$^3$H-9,10]glycerol 3-phosphate for 1-palmitoyl[$^3$H-9,10]glycerol 3-phosphate).

Carnitine O-palmitoyltransferase 1 (CPT1)

CPT1 catalyzes the formation of L-palmitoylcarnitine and coenzyme A from palmitoyl-CoA and L-carnitine. It is located on the external surface of the inner mitochondrial membrane, and much of the control of the rate of hepatic mitochondrial beta-oxidation appears to reside at the level of CPT1, with flux into the mitochondria controlled by effectors of CPT1.

Catalytic Activity

Palmitoyl-CoA+L-carnitine=CoA+L-palmitoylcarnitine

This method of the present invention permits radiometric detection of CPT1 activity via a gain of signal assay partitioning the L-[N-methyl-$^{14}$C]palmitoylcarnitine product of the reaction between L-[N-methyl-$^{14}$C]carnitine and palmitoyl-CoA into the PPSF (Microscint™-E).

Because authentic CPT1 was not available for assay development, radiolabeled substrate and product, ([N-methyl-$^{14}$C]carnitine and [palmitoyl-1-$^{14}$C]palmitoylcarnitine), respectively, were used as controls. A typical 96-well density reaction is partitioned in the following manner: 100 μL assay inhibitor test mix containing substrates or products and buffer components is incubated at room temperature for 1 hour. This incubation is followed by the addition of 10 μL 1-butanol and 10 μL 2% phosphoric acid with the subsequent addition of 150 μL Microscint™-E. Partitioning does not require a specific mixing step, but does require several hours for establishment and is stable for 24 hours. The radioactive [N-methyl-$^{14}$C]carnitine partitions poorly into the organic phase. The amount of radioactivity detected in the PPSF is dependent upon the amount of [palmitoyl-1-$^{14}$C]palmitoylcarnitine in the well. L-[Palmitoyl-1-$^{14}$C] palmitoylcarnitine is used as a substitute for L-[N-methyl-$^{14}$C] palmitoylcarnitine which is not commercially available. These molecules have identical structures and differ only by the location of the radiolabel. The theoretical signal to background of the assay is established by comparing CPMs in the PPSF using equimolar amounts and equal amounts of radiolabeled substrate and product (substitution of L-[palmitoyl-1-$^{14}$C]palmitoylcarnitine for L-[N-methyl-$^{14}$C]palmitoylcarnitine).

Serine C-palmitoyltransferase (SPT)

SPT catalyzes the condensation of serine with palmitoyl-CoA to produce 3-ketodihydrosphingosine (3-ketosphinganine). Coenzyme A and carbon dioxide are byproducts. SPT is responsible for the initial step of de novo sphingolipid synthesis in eucaryotic cells, and spingolipids are essential for cellular growth.

Catalytic Activity

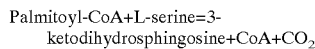
Palmitoyl-CoA+L-serine=3-ketodihydrosphingosine+CoA+$CO_2$

This method of the present invention permits radiometric detection of SPT activity via a gain of signal assay partitioning the D-erythro-[3-$^3$H]ketodihydrosphingosine product of the reaction between L-[3-$^3$H]serine and palmitoyl-CoA into the PPSF (Microscint™-E).

Because authentic SPT was not available for assay development, radiolabeled substrate and a product surrogate, ([3-$^3$H]serine and D-erythro-[3-$^3$H]sphingosine), respectively, were used as controls. A typical 96-well density reaction is partitioned in the following manner: 100 μL assay inhibitor test mix containing substrates or products and buffer components is incubated at room temperature for 1 hour. This incubation is followed by the addition of 150 μL Microscin™-E. Partitioning does not require a specific mixing step, but does require several hours for establishment and is stable for 24 hours. The radioactive ([3-$^3$H]serine partitions poorly into the organic phase. The amount of radioactivity detected in the PPSF is dependent upon the amount of D-erythro-[3-$^3$H]sphingosine in the well. Because radiolableled 3-ketosphinganine is not commercially available, D-erythro-[3-$^3$H]sphingosine is used as a substitute. D-erythro-[3-$^3$H]sphingosine should have similar partitioning characteristics as 3-ketosphinganine. The theoretical signal to background of the assay is established by comparing CPMs in the PPSF using equimolar amounts and equal amounts of radiolabeled substrate and product (substitution of D-rythro-[3-$^3$H]sphingosine for D-erythro-[3-$^3$H]ketodihydrosphingosine).

Methods of Treatment

As used herein, various terms are defined below.

When introducing elements of the present invention or the preferred embodiment(s) thereof, the articles "a," "an," "the," and "said" are intended to mean that there are one or more of the elements.

The terms "comprising," "including," and "having" are intended to be inclusive and mean that there may be additional elements other than the listed elements.

The term "subject" as used herein includes mammals (e.g., humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The term "combination therapy" or "co-therapy" means the administration of two or more therapeutic agents to treat a diabetic condition and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The phrase "therapeutically effective" means the amount of each agent administered that will achieve the goal of improvement in a diabetic condition or disorder severity, while avoiding or minimizing adverse side effects associated with the given therapeutic treatment.

The term "pharmaceutically acceptable" means that the subject item is appropriate for use in a pharmaceutical product.

The compounds identified by the methods of the present invention may be used for the treatment of diabetes, including both type 1 and type 2 diabetes (non-insulin dependent diabetes mellitus). Other diseases and conditions that may be treated or prevented using compounds identified by the methods of the invention include: Maturity-Onset Diabetes of the Young (MODY) (Herman, et al., Diabetes 43:40, 1994); Latent Autoimmune Diabetes Adult (LADA) (Zimmet, et al., Diabetes Med. 11:299, 1994); impaired glucose tolerance (IGT) (Expert Committee on Classification of Diabetes Mellitus, Diabetes Care 22 (Supp. 1):S5, 1999); impaired fasting glucose (IFG) (Charles, et al., Diabetes 40:796, 1991); gestational diabetes (Metzger, Diabetes, 40:197, 1991); and metabolic syndrome X.

The compounds identified by the methods of the present invention may also be effective in such disorders as obesity, and in the treatment of atherosclerotic disease, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease; and for the treatment of lupus, asthma, male reproduction problems, ulcers, sleep disorders, disorders of lipid and carbohydrate metabolism, circadian dysfunction, growth disorders, disorders of energy homeostasis, immune diseases including autoimmune diseases (e.g., systemic lupus erythematosus), as well as acute and chronic inflammatory diseases, and septic shock.

The compounds identified by the methods of the present invention may also be useful for treating physiological disorders related to, for example, cell differentiation to produce lipid accumulating cells, regulation of insulin sensitivity and blood glucose levels, which are involved in, for example, abnormal pancreatic β-cell function, insulin secreting tumors and/or autoimmune hypoglycemia due to autoantibodies to insulin, autoantibodies to the insulin receptor, or autoantibodies that are stimulatory to pancreatic β-cells), macrophage differentiation which leads to the formation of atherosclerotic plaques, inflammatory response, carcinogenesis, hyperplasia, adipocyte gene expression, adipocyte differentiation, reduction in the pancreatic β-cell mass, insulin secretion, tissue sensitivity to insulin, liposarcoma cell growth, polycystic ovarian disease, chronic anovulation, hyperandrogenism, progesterone production, steroidogenesis, redox potential and oxidative stress in cells, nitric oxide synthase (NOS) production, increased gamma glutamyl transpeptidase, catalase, plasma triglycerides, HDL, and LDL cholesterol levels, and the like.

The compounds identified by the methods of the invention may also be used in methods of the invention to treat secondary causes of diabetes (Expert Committee on Classification of Diabetes Mellitus, Diabetes Care 22 (Supp. 1):S5, 1999). Such secondary causes include glucocorticoid excess, growth hormone excess, pheochromocytoma, and drug-induced diabetes. Drugs that may induce diabetes include, but are not limited to, pyriminil, nicotinic acid, glucocorticoids, phenytoin, thyroid hormone, β-adrenergic agents, α-interferon and drugs used to treat HIV infection.

The compounds identified by the methods of the present invention may be used alone or in combination with additional therapies and/or compounds known to those skilled in the art for the treatment of, for example, diabetes and related disorders, obesity, cardiovascular disaes, and cancer.

For example, compounds identified by the methods of the present invention may be administered in combination with other known therapies for the treatment of diabetes, including PPAR ligands (e.g., agonists, antagonists), insulin secretagogues, for example, sulfonylurea drugs and non-sulfonylurea secretagogues, α-glucosidase inhibitors, insulin sensitizers, hepatic glucose output lowering compounds, insulin and insulin derivatives, and anti-obesity drugs. Such therapies may be administered prior to, concurrently with, or following administration of the compounds of the invention. Insulin and insulin derivatives include both long and short acting forms and formulations of insulin. PPAR ligands may include agonists and/or antagonists of any of the PPAR receptors or combinations thereof. For example, PPAR ligands may include ligands of PPAR-α, PPAR-γ, PPAR-δ or any combination of two or three of the receptors of PPAR. PPAR ligands include, for example, rosiglitazone, troglitazone, and pioglitazone. Sulfonylurea drugs include, for example, glyburide, glimepiride, chlorpropamide, tolbutamide, and glipizide. α-glucosidase inhibitors that may be useful in treating diabetes when administered with a compound of the invention include acarbose, miglitol, and voglibose. Insulin sensitizers that may be useful in treating diabetes include PPAR-γ agonists such as the glitazones (e.g., troglitazone, pioglitazone, englitazone, MCC-555, rosiglitazone, and the like) and other thiazolidinedione and non-thiazolidinedione compounds; biguanides such as metformin and phenformin; protein tyrosine phosphatase-1B (PTP-1B) inhibitors; dipeptidyl peptidase IV (DPP-IV) inhibitors; and 11beta-HSD inhibitors. Hepatic glucose output lowering compounds that may be useful in treating diabetes when administered with a compound of the invention include, for example, glucagon anatgonists and metformin, such as Glucophage and Glucophage XR. Insulin secretagogues that may be useful in treating diabetes when administered with a compound of the invention include sulfonylurea and non-sulfonylurea drugs: GLP-1, GIP, PACAP, secretin, and derivatives thereof; nateglinide, meglitinide, repaglinide, glibenclamide, glimepiride, chlorpropamide, and glipizide. For example, GLP-1 includes derivatives of GLP-1 with longer half-lives than native GLP-1, such as, for example, fatty-acid derivatized GLP-1 and exendin.

Compounds identified by the methods of the present invention may also be administered in combination with anti-obesity drugs. Anti-obesity drugs include β-3 agonists; CB-1 antagonists; neuropeptide Y5 inhibitors; Ciliary Neurotrophic Factor and derivatives (e.g., Axokine); appetite suppressants, such as, for example, sibutramine (Meridia); and lipase inhibitors, such as, for example, orlistat (Xenical).

In addition, compounds identified by the methods of the present invention may also be administered in combination with drugs commonly used to treat lipid disorders. Such drugs include, but are not limited to, HMG-CoA reductase inhibitors, nicotinic acid, fatty acid lowering compounds (e.g., acipimox); lipid lowering drugs (e.g., stanol esters, sterol glycosides such as tiqueside, and azetidinones such as ezetimibe), ACAT inhibitors (such as avasimibe), bile acid sequestrants, bile acid reuptake inhibitors, microsomal triglyceride transport inhibitors, and fibric acid derivatives. HMG-CoA reductase inhibitors include, for example, lovastatin, simvastatin, pravastatin, fluvastatin, atorvastatin, rivastatin, itavastatin, cerivastatin, and ZD-4522. Fibric acid derivatives include, for example, clofibrate, fenofibrate, bezafibrate, ciprofibrate, beclofibrate, etofibrate, and gemfibrozil. Sequestrants include, for example, cholestyramine, colestipol, and dialkylaminoalkyl derivatives of a cross-linked dextran.

Furthermore, compounds identified by the methods of the present invention may also be administered combination with anti-hypertensive drugs, such as, for example, β-blockers and ACE inhibitors. Examples of additional anti-hypertensive agents for use in combination with the compounds of the present invention include calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e. g., losartan, irbesartan, valsartan), ET receptor antagonists (e.g., sitaxsentan, atrsentan, neutral endopeptidase (NEP) inhibitors, vasopepsidase inhibitors (dual NEP-ACE inhibitors) (e.g., omapatrilat and gemopatrilat), and nitrates.

Such co-therapies may be administered in any combination of two or more drugs (e.g., a compound identified by the methods of the invention in combination with an insulin sensitizer and an anti-obesity drug). Such co-therapies may be administered in the form of pharmaceutical compositions, as described above.

In another aspect of the invention, compounds identified by the methods described herein may be used to treat or prevent hyper-proliferative disorders. Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The disorders described above have been well characterized in humans, but also exist with a similar etiology in other mammals. Accordingly, the method of this invention can be administered to mammals, including humans, in need thereof for the treatment of angiogenesis and/or proliferative dependent disorders.

The compounds identified by the methods of this invention may be combined with other anti-hyper-proliferative or other indication agents, and the like, as well as with admixtures and combinations thereof. For example, optional anti-hyper-proliferative agents which can be added to the composition include but are not limited to compounds listed on the cancer chemotherapy drug regimens in the 11th Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine. Other anti-hyper-proliferative agents suitable for use include other anti-cancer agents such as epothilone, irinotecan, raloxifen and topotecan.

Other anti-hyper-proliferative agents suitable for use include, but are not limited to, those compounds acknowledged to be used in the treatment and/or prevention of neoplastic diseases in *Goodman and Gilman's The Pharmacological Basis of Therapeutics* (Ninth Edition), editor Molinoff et al., publ. by McGraw-Hill, pages 1225–1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Evaluation of Compounds

Demonstration of the utility of compounds identified by the methods of the present invention may be accomplished through in vitro or in vivo assays that are well known in the art. For example, to demonstrate the efficacy of a pharmaceutical agent for the treatment of cancer, an in vitro tumor cell proliferation assay may be used. The link between activity in tumor cell proliferation assays in vitro and anti-tumor activity in the clinical setting has been very well established in the art. For example, the therapeutic utility of taxol (Silvestrini, et al., Stem Cells 11(6):528–535, 1993), taxotere (Bissery, et al., Anti Cancer Drugs 6(3):339, 1995), and topoisomerase inhibitors (Edelman, et al., Cancer Chemother. Pharmacol. 37(5):385–393, 1996) were demonstrated with the use of in vitro tumor proliferation assays.

To demonstrate the efficacy of a pharmaceutical agent for the treatment of diabetes and related disorders such as Syndrome X, impaired glucose tolerance, impaired fasting glucose, and hyperinsulinemia or atherosclerotic disease and related disorders such as hypertriglyceridemia and hypercholesteremia, the following assays may be used.

Insulin Receptor Binding in 3T3-L1 Cells Treated with Compounds

3T3-L1 cells are seeded at 9300 cells per well in Costar flat bottom TC and incubated for 1 week until they are 2 days post-confluent (e.g., cells have reached maximum density). The cells are then treated for 2 days with differentiation media (Dulbecco's Modified Eagle Medium (DMEM), 100 $\mu$g/ml Penicillin/Streptomycin, 2 mM L-Glutamine, 10% Fetal Bovine Serum) containing 0.5 $\mu$M human Insulin-like Growth Factor (IGF-1) and test compounds. After treatment, the media is replaced with differentiation media, and the cells are incubated for 4 days. The cells are then assayed for insulin receptor activity. After washing the cells with buffer, they are incubated with 0.1 nM $^{125}$I-insulin and (+/−) 100 nM unlabeled insulin, and incubated at rt for 1 hour. The cells are then washed 3× with buffer, dissolved with 1N NaOH, and counted on a gamma counter. An $EC_{50}$ value is determined if a plateau was attained and percent maximum stimulation is assessed.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 14 days. At this point, the animals are bled again by eye or tail vein and blood glucose levels are determined. In each case, glucose levels are measured with a Glucometer Elite XL (Bayer Corporation, Elkhart, Ind.).

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 8 days. The animals are then bled again by eye or tail vein, and serum triglyceride levels are determined. In each case, triglyceride levels are measured using a Technicon Axon Autoanalyzer (Bayer Corporation, Tarrytown, N.Y.).

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 days, and then bled again on day 8. Plasma is analyzed for HDL-cholesterol using the Synchron Clinical System (CX4) (Beckman Coulter, Fullerton, Calif.).

Method for Measuring Total Cholesterol, HDL-Cholesterol, Triglycerides, and Glucose Levels In another in vivo assay, obese monkeys are bled, then orally dosed once daily with vehicle or test compound for 4 weeks, and then bled again. Serum is analyzed for total cholesterol, HDL-cholesterol, triglycerides, and glucose using the Synchron Clinical System (CX4) (Beckman Coulter, Fullerton, Calif.). Lipoprotein subclass analysis is performed by NMR spectroscopy as described by Oliver et al., (Proc. Natl. Acad. Sci. USA 98:5306–5311, 2001).

Method for Measuring an Effect on Cardiovascular Parameters

Cardiovascular parameters (e.g., heart rate and blood pressure) are also evaluated. SHR rats are orally dosed once daily with vehicle or test compound for 2 weeks. Blood pressure and heart rate are determined using a tail-cuff method as described by Grinsell et al., (Am. J. Hypertens. 13:370–375, 2000). In monkeys, blood pressure and heart rate are monitored as described by Shen et al., (J. Pharmacol. Exp. Therap. 278:1435–1443, 1996).

In vitro Tumor Cell Proliferation Assay

The tumor cell proliferation assay used to test the activity of compounds involves a readout called Cell Titer-Glow® Luminescent Cell Viability Assay developed by Promega (Madison, Wis.) (Cunningham, The Scientist 15(13):26, 2001; Crouch, et al., J. Immunol. Methods 160:81–88, 1993), that measures inhibition of cell proliferation. Generation of a luminescent signal corresponds to the amount of ATP present, which is directly proportional to the number of metabolically active (proliferating) cells.

A431cells (human epidermoid, ATCC, Manassas, Va.) are plated at a density of $2.5 \times 10^3$ cells/well in 96 well black-clear bottom tissue culture plates in complete media with 10% Fetal Calf Serum and incubated at 37° C. Twenty-four hours later, test compounds are added in serial dilutions. Cells are incubated for 72 hours at 37° C. in complete growth media after addition of the test compound. After 72 hours of drug exposure, the plates are equilibrated to room temperature for approximately 30 minutes. Then, using a Promega Cell Titer Glo Luminescent® assay kit, lysis buffer containing 100 μl of the enzyme luciferase and its substrate, luciferin mixture, is added to each well. The plates are mixed for 2 minutes on orbital shaker to ensure cell lysis, and incubated for 10 minutes at room temperature to stabilize luminescence signal. The samples are read on a luminometer (VICTOR 2 using Luminescence protocol), and analyzed with Analyze5 using a 4 parameter fit to measure the amount of ATP present in the cell lysates from each well, which corresponds to the number of viable cells in that well. For determination of $IC_{50}$'s, a linear regression analysis may be used to determine drug concentration which results in a 50% inhibition of cell proliferation using this assay format.

Pharmaceutical Compositions

As used herein, various terms are defined below.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "subject" as used herein includes mammals (e.g., humans and animals).

The term "treatment" includes any process, action, application, therapy, or the like, wherein a subject, including a human being, is provided medical aid with the object of improving the subject's condition, directly or indirectly, or slowing the progression of a condition or disorder in the subject.

The term "combination therapy" or "co-therapy" means the administration of two or more therapeutic agents to treat a diabetic condition and/or disorder. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner.

The phrase "therapeutically effective" means the amount of each agent administered that will achieve the goal of improvement in a disease condition or disorder severity, while avoiding or minimizing adverse side effects associated with the given therapeutic treatment.

The term "pharmaceutically acceptable" means that the subject item is appropriate for use in a pharmaceutical product.

Based on the above tests, or other well known assays used to determine the efficacy for treatment of conditions identified above in mammals, and by comparison of these results with the results of known medicaments that are used to treat these conditions, the effective dosage of the compounds identified by the methods of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound may be ascertained by those skilled in the art using conventional treatment tests.

The compounds identified by the methods of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a pharmaceutically effective amount of a compound identified by the methods described herein, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound is that amount which produces a result or exerts an influence on the particular condition being treated. The compounds identified by the methods described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds identified by the methods of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

Pharmaceutical compositions may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds identified by the methods of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly(ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

Pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

Pharmaceutical composition may also be administered in the form of suppositories for rectal administration of the drug. These compositions may be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

Pharmaceutical compositions may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC$—$CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., carnuba wax and white wax); thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds identified by the methods described herein may be administered as the sole pharmaceutical agent or in combination with one or more other pharmaceutical agents where the combination causes no unacceptable adverse effects. For example, compounds be combined with known anti-obesity, or with known antidiabetic or other indication agents, and the like, as well as with admixtures and combinations thereof.

The compounds identified by the methods described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000).

It should be apparent to one of ordinary skill in the art that changes and modifications can be made to this invention without departing from the spirit or scope of the invention as it is set forth herein.

We claim:

1. A method for measuring enzyme activity of a reaction comprising
    combining an enzyme and radiolabeled substrate(s);
    adding a phase-partition scintillation fluid;
    incubating the reaction for at least two hours; and
    detecting enzyme activity,
wherein said reaction does not require mixing following addition of the phase-partition scintillation fluid and wherein said reaction is conducted in a single reaction vessel.

2. The method of claim 1, further comprising
    terminating the reaction by acidification.
3. The method of claim 1, wherein the reaction is conducted in organic resistant multiwell plates.
4. The method of claim 3, wherein the multiwell plate comprises up to 96 wells.
5. The method of claim 3, wherein the multiwell plate comprises greater than 96 wells.
6. The method of claim 3, wherein the multiwell plate comprises up to 384 wells.
7. The method of claim 3, wherein the multiwell plate comprises greater than 384 wells.
8. The method of claim 1, wherein said method is used for high throughput screening.
9. The method of claim 1, wherein said enzyme is selected from fatty acid synthase; acetyl CoA carboxylase; diacyiglycerol acetyltransferase; farnesyl diphosphate synthase; glycerol-3-phosphate O-acyltransferase; carnitine O-palmitoyltransferase 1; serine C-palmitoyltransferase; or phospholipase C gamma.
10. The method of claim 1, comprising measuring enzyme activity by radiometric detection.
11. The method of claim 1, wherein enzyme activity is measured by incorporation of a radiolabel-containing moiety into product molecules or loss of a radiolabel-containing moiety into substrate molecules.
12. The method of claim 2, wherein an acid is selected from acetic acid, phosphoric acid, or hydrochloric acid.
13. A method for identifying compounds that modulate enzyme activity in a reaction comprising
    combining an enzyme, radiolabeled substrate(s) and test compounds;
    adding a phase-partition scintillation fluid;
    incubating the reaction for at least two hours; and
    detecting enzyme activity,
wherein said reaction does not require mixing following addition of the phase-partition scintillation fluid and wherein said reaction is conducted in a single reaction vessel.

14. The method of claim 13, further comprising
    terminating the reaction by acidification.
15. The method of claim 13, wherein the reaction is conducted in organic resistant multiwell plates.
16. The method of claim 15, wherein the multiwell plate comprises up to 96 wells.
17. The method of claim 15, wherein the multiwell plate comprises greater than 96 wells.
18. The method of claim 15, wherein the multiwell plate comprises up to 384 wells.
19. The method of claim 15, wherein the multiwell plate comprises greater than 384 wells.
20. The method of claim 13, wherein said method is used for high throughput screening.
21. The method of claim 13, wherein said enzyme is selected from fatty acid synthase; acetyl CoA carboxylase; diacylglycerol acetyltransferase; farnesyl diphosphate synthase; glycerol-3-phosphate O-acyltransferase; camitine O-palmitoyltransferase 1; serine C-palmitoyltransferase; or phospholipase C gamma.
22. The method of claim 13, comprising measuring enzyme activity by radiometric detection.
23. The method of claim 13, wherein enzyme activity is measured by incorporation of a radiolabel-containing moiety into product molecules or loss of a radiolabel-containing moiety into substrate molecules.
24. The method of claim 14, wherein an acid is selected from acetic acid, phosphoric acid, or hydrochloric acid.

* * * * *